United States Patent [19]

Makino et al.

[11] Patent Number: 5,676,811
[45] Date of Patent: Oct. 14, 1997

[54] AIR-FUEL RATIO DETECTING DEVICE

[75] Inventors: Daisuke Makino, Ichinomiya; Hisayoshi Ohta, Okazaki; Keigo Mizutani, Nishio; Masataka Naito, Kariya; Masanori Yamada, Nishio; Masahiro Shibata, Nagoya; Hiromi Sano, Nagoya, all of Japan

[73] Assignees: Nippondenso Co., Ltd., Kariya; Nippon Soken, Inc., Nishio, both of Japan

[21] Appl. No.: 789,709

[22] Filed: Jan. 27, 1997

Related U.S. Application Data

[63] Continuation of Ser. No. 547,551, Oct. 24, 1995, abandoned.

[30] Foreign Application Priority Data

Oct. 24, 1994 [JP] Japan ................................ 6-258013
Aug. 9, 1995 [JP] Japan ................................ 7-203167

[51] Int. Cl.$^6$ ............................................................ G01N 27/26
[52] U.S. Cl. ........................... 204/425; 204/426; 204/427; 204/429
[58] Field of Search ................................. 204/425, 426, 204/427, 429

[56] References Cited

U.S. PATENT DOCUMENTS

| | | | |
|---|---|---|---|
| 4,282,080 | 8/1981 | Muller et al. | 204/195 S |
| 4,579,643 | 4/1986 | Mase et al. | 204/427 |
| 4,647,364 | 3/1987 | Mase et al. | 204/427 |
| 4,670,128 | 6/1987 | Mase et al. | 204/427 |
| 4,718,999 | 1/1988 | Suzuki et al. | 204/406 |
| 4,755,274 | 7/1988 | Mase et al. | 204/427 |
| 4,824,548 | 4/1989 | Iino et al. | 204/406 |
| 4,859,307 | 8/1989 | Nishizawa et al. | 204/429 |
| 4,927,517 | 5/1990 | Mizutani et al. | 204/425 |
| 4,943,330 | 7/1990 | Iino et al. | 156/89 |
| 4,990,235 | 2/1991 | Chujo | 204/429 |
| 5,064,693 | 11/1991 | Hayakawa et al. | 204/429 |
| 5,360,528 | 11/1994 | Oh et al. | 204/425 |

FOREIGN PATENT DOCUMENTS

| | | |
|---|---|---|
| 227 257 | 7/1987 | European Pat. Off. . |
| 59-163558 | 9/1984 | Japan . |
| 62-115356 | 5/1987 | Japan . |
| 62-146956 | 9/1987 | Japan . |
| 5-027822 | 4/1993 | Japan . |
| 5-149920 | 6/1993 | Japan . |
| 6-068483 | 8/1994 | Japan . |
| 6-213864 | 8/1994 | Japan . |

OTHER PUBLICATIONS

Soejima et al: "Multi–Layered Zirconia Oxygen Sensor for Lean Burn Engine Application", 1986 Society of Automotive Engineers, Inc., pp. 3163–3168. no month available.

*Primary Examiner*—Bruce F. Bell
*Attorney, Agent, or Firm*—Cushman, Darby & Cushman IP Group of Pillsbury Madison & Sutro LLP

[57] ABSTRACT

An air-fuel ratio detecting element is composed of an oxygen pump portion and an oxygen sensor portion which are provided on a single solid electrolyte sheet, a heating element, and a spacer. The oxygen pump portion is composed of a pair first of electrodes provided on opposite sides of the solid electrolyte sheet, and a communication hole which is formed through the solid electrolyte sheet and the electrodes. Electrodes are disposed on the solid electrolyte sheet on the same side as the second electrode, whereby the oxygen sensor portion is formed. The spacer has an opening and a slit-like opening. The heating element 4, the spacer, and the solid electrolyte sheet are stacked from bottom to top, and then the stacked assembly is baked. In this case, they are stacked such that the opening faces the first electrodes and the second electrode. By disposing the oxygen pump portion and the oxygen sensor portion on the same solid electrolyte sheet, structure can be made simpler compared with a conventional air-fuel ratio detecting element in which a solid electrolyte sheet is used for each of an oxygen pump portion and an oxygen sensor portion.

20 Claims, 23 Drawing Sheets

AIR-FUEL RATIO DETECTING DEVICE

This is a continuation of application No. 08/547,551, filed on Oct. 24, 1995, now abandoned.

BACKGROUND OF THE INVENTION

1. Field of the Invention

The present invention relates to an air-fuel ratio detecting device.

2. Description of the Related Art

Conventionally, an air-fuel ratio detecting device, which includes an air-fuel ratio detecting element utilizing the principle of an oxygen concentration cell, is used to measure an oxygen concentration in controlling an air-fuel ratio for an internal combustion engine. Such an air-fuel ratio detecting element is proposed, for example, in SAE (Society of Automotive Engineers) Paper 850378.

The air-fuel ratio detecting element proposed in SAE Paper 850378 will now be described with reference to FIG. 21.

An air-fuel ratio detecting element 1 is primarily composed of an oxygen pump portion 2, an oxygen sensor portion 3, and a heating element 4 for heating the oxygen pump portion 2 and the oxygen sensor portion 3. The oxygen pump portion 2 is composed of an oxygen ion conductive solid electrolyte 6 which is formed of stabilized zirconia or the like, and electrodes 7, 8 which are formed on opposite sides of the solid electrolyte 6. The oxygen sensor portion 3 is composed of a solid electrolyte 11 similar to that of the oxygen pump portion 2 and electrodes 12, 13 which are formed on opposite sides of the solid electrolyte 11.

A first spacer 5 formed of an insulating material is disposed between the oxygen pump portion 2 and the oxygen sensor portion 3, whereby an inner space 17 is defined. The inner space 17 communicates with gas to be measured through a communication hole 9 which serves as diffusion resisting means. On the other hand, a second spacer 49 formed of an insulating material is disposed between the oxygen sensor portion 3 and the insulating heater 4, whereby an air passage 19 is formed for leading air thereinto. That is, the oxygen pump portion 2, the spacer 5, the oxygen sensor portion 3, the spacer 49, and the heating element 4 are stacked one another in this order.

Gas to be measured is led in the inner space 17 through the communication hole 9. When a voltage is applied to the oxygen pump portion 2 so as to maintain an electromotive force in the oxygen sensor portion 3 at a fixed level or to obtain a predetermined oxygen concentration in the inner space 17 which communicates with gas to be measured, oxygen ions move within the solid electrolyte 6. At this time, the current which flows through the oxygen pump portion 2 is correlated with the concentration of oxygen in gas to be measured. Accordingly, the concentration of oxygen in gas to be measured can be detected based on the magnitude of the current which flows through the oxygen pump portion 2.

This conventional air-fuel ratio detecting element has a disadvantage of a complex structure because the oxygen pump portion 2 and the oxygen sensor portion 3 are constructed of separate solid electrolytes 6, 11.

SUMMARY OF THE INVENTION

A primary object of the present invention is to provide an air-fuel ratio detecting device which has a simplified structure, and which can be manufactured at reduced costs.

According to an aspect of the present invention, there is provided an air-fuel ratio detecting device in which an oxygen pump portion and an oxygen sensor portion are formed on the same solid electrolyte sheet. Therefore, the number of solid electrolyte sheets can be reduced compared with the case where the oxygen pump portion and oxygen sensor portion are constructed of separate solid electrolyte sheets, thereby making the overall structure simpler and reducing costs of manufacture of solid electrolyte sheets as well as costs of materials.

According to another aspect of the present invention, each of the oxygen pump portion and the oxygen sensor portion has a pair of electrodes, thereby providing an advantage in routing electric signals.

According to yet another aspect of the present invention, in addition to disposing the oxygen pump portion and the oxygen sensor portion on the same solid electrolyte sheet, a heating element is provided. Therefore, the oxygen pump portion and the oxygen sensor portion can be heated together, whereby these two portions can be heated uniformly and thus activated more quickly.

According to a further aspect of the present invention, a communication hole is formed in the solid electrolyte sheet for establishing communication between an inner space and gas to be measured. Therefore, by selecting the size and the number of communication holes, a flow of gas to be measured into the inner space can be controlled easily.

According to still another aspect of the present invention, a reference oxygen space and an inner space communicating with gas to be measured are both defined between the solid electrolyte sheet and an insulating sheet. Thus, compared with the case where one space is defined between a solid electrolyte sheet and an insulating sheet and where another space is defined on the opposite side of the solid electrolyte sheet between the solid electrolyte sheet and an additional insulating sheet, such additional insulating sheet is not required for defining both spaces. This avoids an increase in device thickness, whereby the overall structure can be made more compact.

Also, by disposing an isolating member between the solid electrolyte sheet and the insulating sheet, the reference oxygen space and the inner space can be reliably isolated from each other, whereby a leak between the spaces can be prevented.

According to a still further aspect of the present invention, the oxygen pump portion and the oxygen sensor portion are formed on the same side of the solid electrolyte sheet. Thus, their electrodes can be formed on the solid electrolyte sheet in one process, thereby providing easier in manufacture.

According to yet another aspect of the present invention, a slit is formed in the solid electrolyte sheet across its width between the oxygen pump portion and the oxygen sensor portion, the slit being shorter than the width of the solid electrolyte sheet. The slit functions to improve the electrical insulating performance between the oxygen pump portion and the oxygen sensor portion, whereby a leak current can be prevented from flowing therebetween.

According to a still further aspect of the present invention, a volume adjusting means is fixed on an insulating sheet in such a manner that it faces the inner space, whereby the volume of the inner space is adjusted. With this structure, by reducing the volume of the inner space, time required for the oxygen pump portion to take gas to be measured into and out from the inner space can be reduced, whereby response to a change in the concentration of oxygen in gas to be measured can be improved.

According to another aspect of the present invention, the reference oxygen space and the inner space are defined between a heating element sheet and the solid electrolyte sheet. Thus, compared with the case where separate electrical insulating ceramic substrates are used for defining the reference oxygen space and the inner space and where a heating element sheet is combined therewith, heat generated by the heating element sheet can be transmitted more effectively to the solid electrolyte sheet.

DESCRIPTION OF THE PREFERRED EMBODIMENTS

First embodiment:

An air-fuel ratio detecting element according to a first embodiment of the present invention will now be described with reference to FIG. 1 and FIG. 2.

Figure 1:
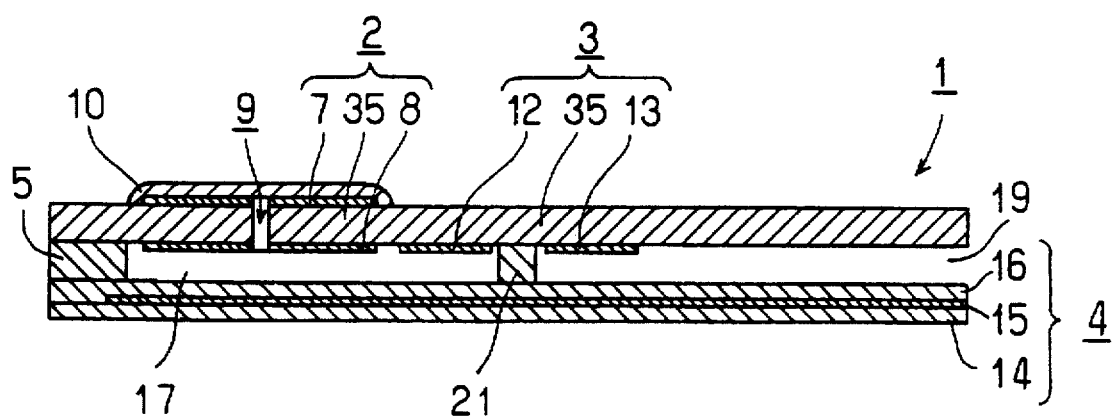
FIG. 1 is a schematic cross-sectional view of an air-fuel ratio detecting element according to a first embodiment of the present invention.
Figure 2:
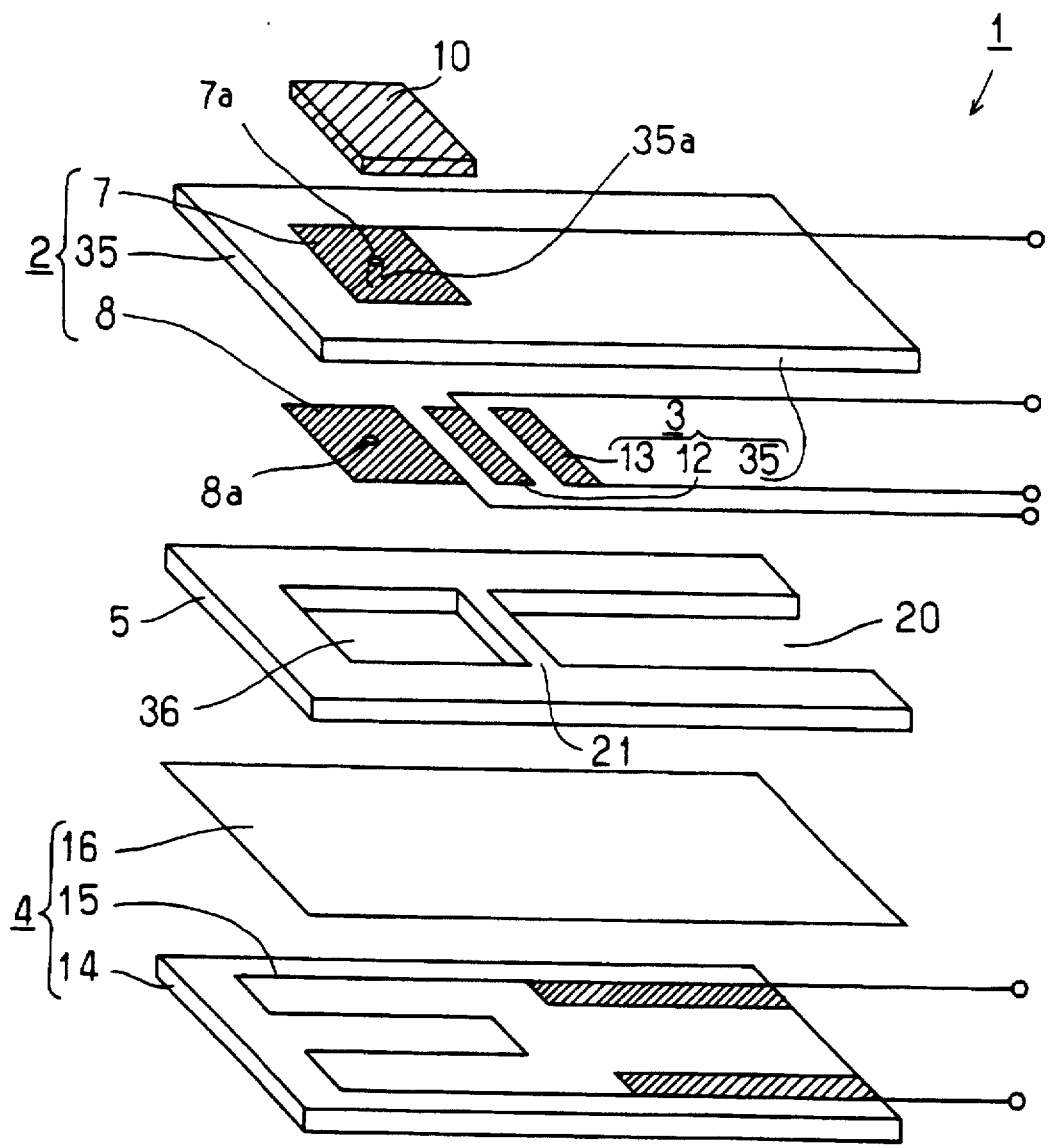
FIG. 2 is a schematic exploded view of the air-fuel ratio detecting element according to the first embodiment of the present invention.

As shown in FIGS. 1 and 2, the air-fuel ratio detecting element 1 of the present embodiment is composed of a heating element 4, a spacer 5, and an oxygen pump portion 2 and an oxygen sensor portion 3 which are provided on a common solid electrolyte sheet 35.

Electrodes 7, 8 made of a catalytic metal such as platinum and the like are formed by screen-printing on opposite sides of the flat solid electrolyte sheet 35 made of yttria-added zirconia, whereby the oxygen pump portion 2 is formed. The solid electrolyte sheet 35 is formed by a doctor blade method or a similar sheet forming method. The solid electrolyte sheet 35 can be within the range of 50 to 300 μm in thickness, preferably within the range of 100 to 200 μm, in view of balance between electric resistance and sheet strength. The electrodes 7, 8 can be within the range of 1 to 20 μm in thickness, preferably within the range of 5 to 10 μm in view of heat resistance and gas diffusibility. The solid electrolyte sheet 35 has a hole 35a, and the electrodes 7, 8 have holes 7a, 8a, respectively, the holes being positioned so as to align with each other. The holes 35a, 7a, 8a form a communication hole 9 which passes through the oxygen pump portion 2 and serves as diffusion resisting means. To prevent the communication hole 9 from being clogged with powder such as soot contained in gas to be measured, a porous ceramic protector 10 is provided so as to cover the entire electrode 7. The protector 10 is formed by applying and baking a porous paste which is prepared from a ceramic insulating material such as alumina.

Furthermore, electrodes 12, 13 are screen-printed apart from each other on the solid electrolyte sheet 35 on the same side as the electrode 8, whereby the oxygen sensor portion 3 is formed. That is, the oxygen pump portion 2 and the oxygen sensor portion 3 are formed on the same solid electrolyte sheet 35. The electrodes 12, 13 are identical in material with the electrodes 7, 8 of the oxygen pump portion 2.

The sheet-like heating element 4 is composed of a substrate 14 which is made of a ceramic insulating material such as alumina, an electrical heating member 15 which is formed by screen-printing an electrical resisting material such as platinum on the surface of the substrate 14, and a substrate 16 which covers the electrical heating member 15 and is made of a ceramic insulating material.

The spacer 5 has a flat U-like shape and is made of a ceramic insulating material such as alumina. The spacer 5 has a slit which extends in a longitudinal direction at the laterally central portion thereof from a portion, which faces the electrode 13 of the oxygen sensor portion 3 when united, to one end thereof. This slit serves as an opening 20 which forms an air passage 19 where air serving as a reference oxygen substance is present. Also, the spacer 5 has an opening 36 between another end thereof and the opening 20. The opening 36 forms an inner space 17 which is large enough to accommodate the electrode 8 and the electrode 12 provided on the solid electrolyte sheet 35 when stacked. In addition, the spacer 5 has a partition 21 between the opening 36 and the opening 20 so as to separate the inner space 17 from the air passage 19 when stacked.

The spacer 5 is superposed on the solid electrolyte sheet 35 on the same side as the electrodes 8, 12, 13. At this time, the spacer 5 is placed in such a manner that the opening 36 faces the electrodes 8, 12 and that the opening 20 faces the electrode 13. The heating element 4 is superposed on the spacer 5 via a substrate 16. Thus, the heating element 4, the spacer 5, and the solid electrolyte sheet 35 provided with the oxygen pump portion 2 and the oxygen sensor portion 3 are stacked from bottom to top in FIGS. 1 and 2. Then, the stacked assembly is united by thermocompression bonding and then baked. Thus, as shown in FIG. 1, the inner space 17 and the air passage 19 are formed.

A manufacturing method for the air-fuel ratio detecting element 1 will next be described.

Many solid electrolyte sheets 35, spacers 5, and substrates 14 and 16 for heating elements 4 are first respectively connected longitudinally and laterally. Electrodes 7, 8, 12, 13 are screen-printed on the solid electrolyte sheets 35, and electrical heating members 15 are screen-printed on the substrates 14 for the heating elements 4. Then, the substrates 14 for the heating elements 4, the substrates 16 for the heating elements 4, the spacers 5, and the solid electrolyte sheets 35 are stacked from bottom to top, and united by thermocompression bonding. The bonded assembly is baked and then divided into individual pieces. Thus, a large quantity of air-fuel ratio detecting elements 1 can be manufactured at a time in one process. This method is quite efficient and achieves low-cost mass production.

Here, the effects obtained from the structure of the first embodiment will now be described.

First, since the oxygen pump portion 2 and the oxygen sensor portion 3 are disposed on the same solid electrolyte sheet 35, the number of solid electrolyte sheets 35 can be reduced, whereby the overall structure can be simplified. Also, since the number of solid electrolytes 35 decreases, the overall heat capacity can be reduced, and thus the heating element 4 can heat the solid electrolyte sheet 35 at a higher efficiency. That is, the temperature of the air-fuel ratio detecting element 1 can be raised quicker (quicker activation). Since the oxygen pump portion 2 and the oxygen sensor portion 3 can be heated together, they can be uniformly heated. This also contributes to quicker activation of the air-fuel ratio detecting element 1. Furthermore, the costs of manufacture and materials for the solid electrolyte sheet 35 can be reduced.

As a result of reducing the number of solid electrolyte sheets 35, the number of member-to-member bonding surfaces reduces, whereby separation between members caused by differences in coefficient of contraction and coefficient of thermal expansion between them is less likely to occur during baking and use. This reduces defectives.

Second, there is provided the heating element 4 which is composed of the substrate 14 serving as an insulating sheet, the electrical heating member 15, and the substrate 16. The heating element 4 functions as a ceramic insulating sheet for defining, in cooperation with the solid electrolyte sheet 35, the inner space 17 and the air passage 19. This structure, therefore, can transmit heat to the solid electrolyte sheet 35 more effectively than an imaginary structure where a separate substrate is provided to form the inner space 17 and the air passage 19, and the heating element 4 is disposed on the substrate.

Third, the inner space 17 communicates with gas to be measured through the communication hole which is formed through the solid electrolyte sheet 35 in the direction of thickness and which serves as a communicating means. When an atmosphere of gas to be measured changes, the gas has a new atmosphere must be led into the inner space 17. The communication hole 9 can finely control the inflow amount of gas to be measured. For example, it is possible to provide a plurality of communication holes 9.

Fourth, the air passage 19 and the inner space 17 are defined between the solid electrolyte sheet 35 and the heating element 4 (insulating sheet). Also, the spacer 5 which has the openings 20, 36 for defining the air passage 19 and the inner space 17, and the partition 21 for separating the openings 20 and 36 from each other is disposed between the solid electrolyte sheet 35 and the heating element 14.

Fifth, the electrodes 7, 8 of the oxygen pump portion 2 are formed on opposite sides of the solid electrolyte sheet 35. That is, the electrode 8 is formed on a first side facing the heating element 4, while the electrode 7 is formed on a second side which is exposed to gas to be measured. Also, the mutually separated electrodes 12, 13 of the oxygen sensor portion 3 are formed on the first side of the solid electrolyte sheet 35.

With the fourth and fifth structural features, the inner space 17 and the air passage 19 can easily and concurrently be formed by arranging the solid electrolyte sheet 35 and the heating element 4 such that they are opposed to each other and by disposing the spacer 5 between them. This advantage is enhanced further by forming a pair of electrodes 12, 13 of the oxygen sensor portion 3 on the first side of the solid electrolyte sheet 35 where the electrode 8 of the oxygen pump portion 2 is formed.

The structure described above is advantageous to manufacture. Since the inner space 17 and the air passage 19 are defined in the same plane, the overall dimension of layers in the direction of thickness of the solid electrolyte sheet 35 can be made smaller as compared with the case where the air passage 19 is defined on the second side (exposed to gas to be measured) of the solid electrolyte sheet 35, for example. As a result, the air-fuel ratio detecting element can be made more compact as a whole. Also, the partition 21 reliably separates the air passage 19 from the inner space 17, whereby gas leakage between them can be prevented.

Also, since the protector 10 is provided so as to cover the electrode 7 having the communication hole 9, the communication hole 9 can be prevented from being clogged with solid components (carbon for example) contained in gas to be measured, and also the electrode 7 can be prevented from being deteriorated by phosphorous, sulfur and the like contained in gas to be measured.

Figure 3:
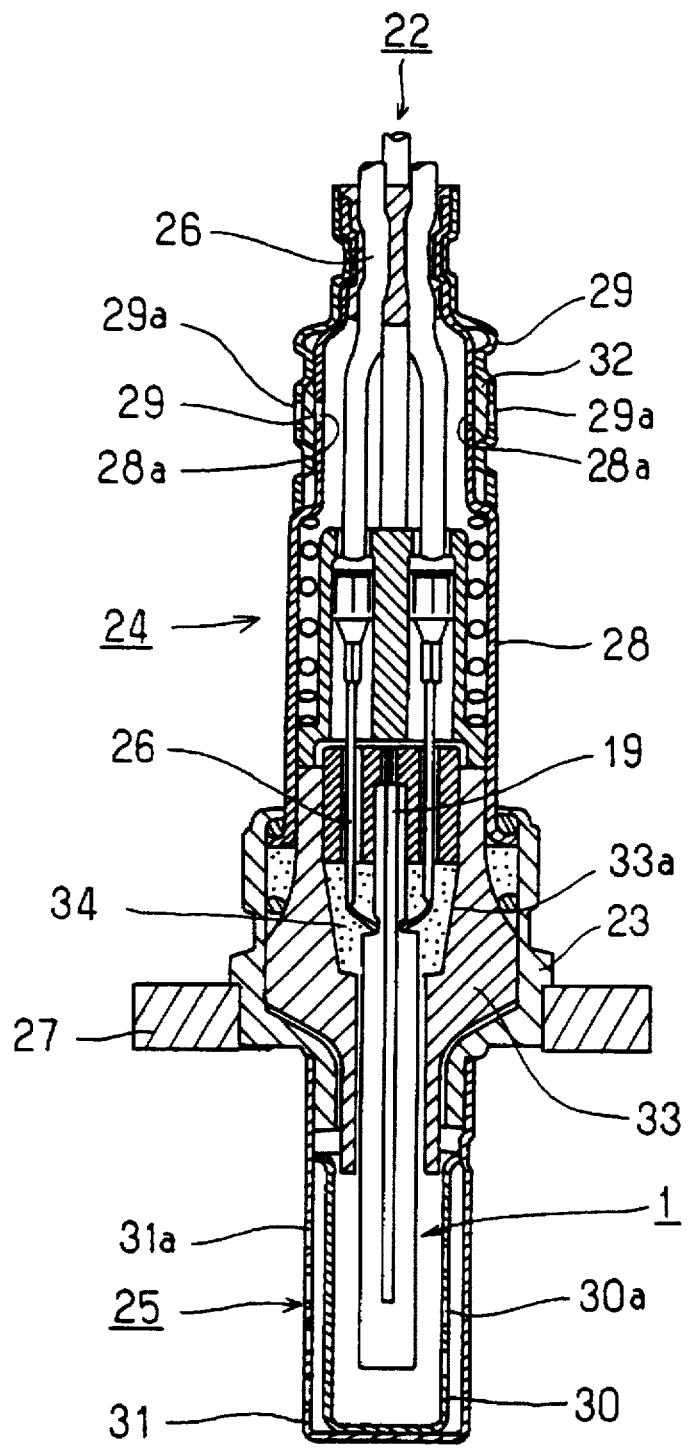
FIG. 3 is a cross-sectional view of an air-fuel ratio detecting device in which an air-fuel ratio detecting element of the present invention is mounted.

The structure of an air-fuel ratio detecting device 22 which uses the air-fuel ratio detecting element 1 of FIG. 1 will now be described with reference to FIG. 3.

The air-fuel ratio detecting device 22 is composed of a housing 23 which contains the air-fuel ratio detecting element 1, an air cover 24 which is in contact with the air, and an exhaust cover 25 which is inserted into an exhaust passage. Lead wires 26 are disposed on both sides of the rear end of the air-fuel ratio detecting element 1 at which the air passage 19 exists. The air-fuel ratio detecting element 1 is inserted into a through-hole 33a formed in an insulating member 33. The space between the air-fuel ratio detecting element 1 and the insulating member 33 is filled with an insulating sealant 34, whereby the air-fuel ratio detecting element 1 is fixed to the insulating member 33 and housed in the housing 23. A circular flange 27 is provided on the housing 23 at a central portion thereof. The air cover 24 is attached to one end of the housing 23 at which the air passage 19 of the air-fuel ratio detecting element 1 exists. The exhaust cover 25 is attached to the housing 23 at the other end.

The air cover 24 is composed of a main cover 28 which is attached to the housing 23 and a sub-cover 29 which covers the rear end of the main cover 28. The main cover 28 and the sub-cover 29 have air ports 28a and 29a, respectively, for taking the air in the air cover 24 in order to measure a reference oxygen concentration. A water repellent filter 32 is inserted between air ports 28a of the main cover 28 and air ports 29a in the sub-cover 29 for waterproofing. Accordingly, the air can enter the air-fuel ratio detecting device 22, but water cannot.

The air cover 24 is open at both ends. The lead wires 26 which are connected to the air-fuel ratio detecting element 1 by brazing or the like are led out from the air cover 24 at an end opposite to the housing 23.

The exhaust cover 25 is composed of an inner cover 30 and an outer cover 31, both made of stainless steel, thereby providing a dual-sleeve structure. Both the inner and outer covers 30, 31 have exhaust gas ports 30a and 31a, respectively, for taking exhaust gas into the exhaust cover 25.

The operation of the first embodiment will now be described.

The exhaust cover 25 of the air-fuel ratio detecting device 22 is inserted into an exhaust passage of an automobile engine. The air-fuel ratio detecting device 22 takes exhaust into the exhaust cover 25 through the exhaust gas ports 30a, 31a, whereby the oxygen pump portion 2 of the air-fuel ratio detecting element 1 takes exhaust gas into the inner space 17. On the other hand, the air-fuel ratio detecting device 22 takes the air into the air cover 24 through the air ports 28a, 29a, whereby the air is led into the air passage 19 of the air-fuel ratio detecting element 1.

Thus introduced air is used as gas having a reference oxygen concentration. On the other hand, gas to be measured is taken into the inner space 17 through the communication hole 9. The oxygen sensor portion 3 outputs a sensor voltage corresponding to an electromotive force produced due to the difference between the concentration of oxygen in the air passage 19 and the concentration of oxygen in gas to be measured in the inner space 17. A voltage is applied to the oxygen pump portion 2 so as to make the output of the oxygen sensor portion 3 constant, i.e. maintain the concentration of oxygen at a predetermined level in the inner space 17 which communicates with gas to be measured, whereby oxygen is taken into the inner space 17 from the outer space where gas to be measured exists or taken out from the inner space 17 to the outer space. This movement of oxygen (oxygen ions) causes current to flow through the oxygen pump portion 2. The value of this current is correlated with the concentration of oxygen in gas to be measured. Accordingly, by measuring the value of the current flowing through the oxygen pump portion 2, the concentration of oxygen in gas to be measured can be detected.

Second embodiment:

An air-fuel ratio detecting element according to a second embodiment of the present invention will now be described with reference to FIG. 4 and FIG. 5. In the air-fuel ratio detecting element of the present embodiment, the volume of the inner space 17 of the oxygen pump portion 2 is reduced by a volume adjusting member 44 serving as a volume adjusting means.

Figure 4:
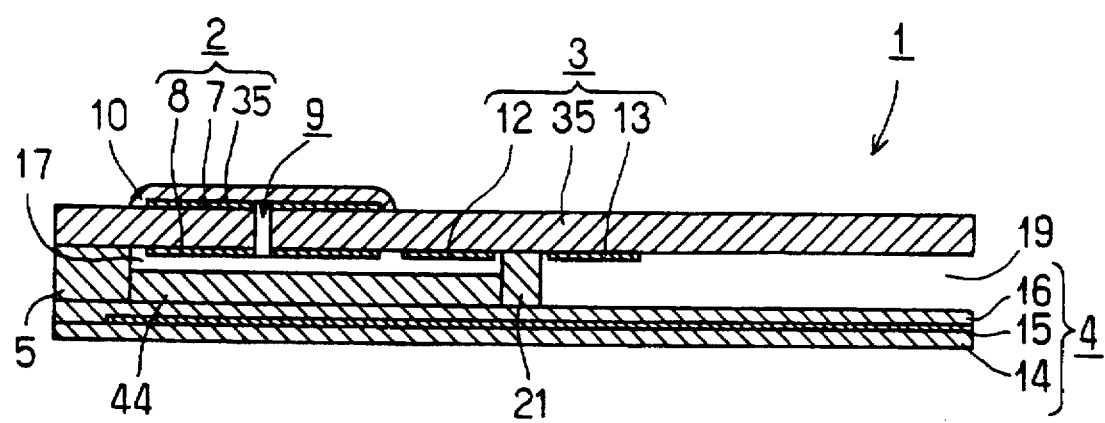
FIG. 4 is a schematic cross-sectional view of an air-fuel ratio detecting element according to a second embodiment of the present invention.
Figure 5:
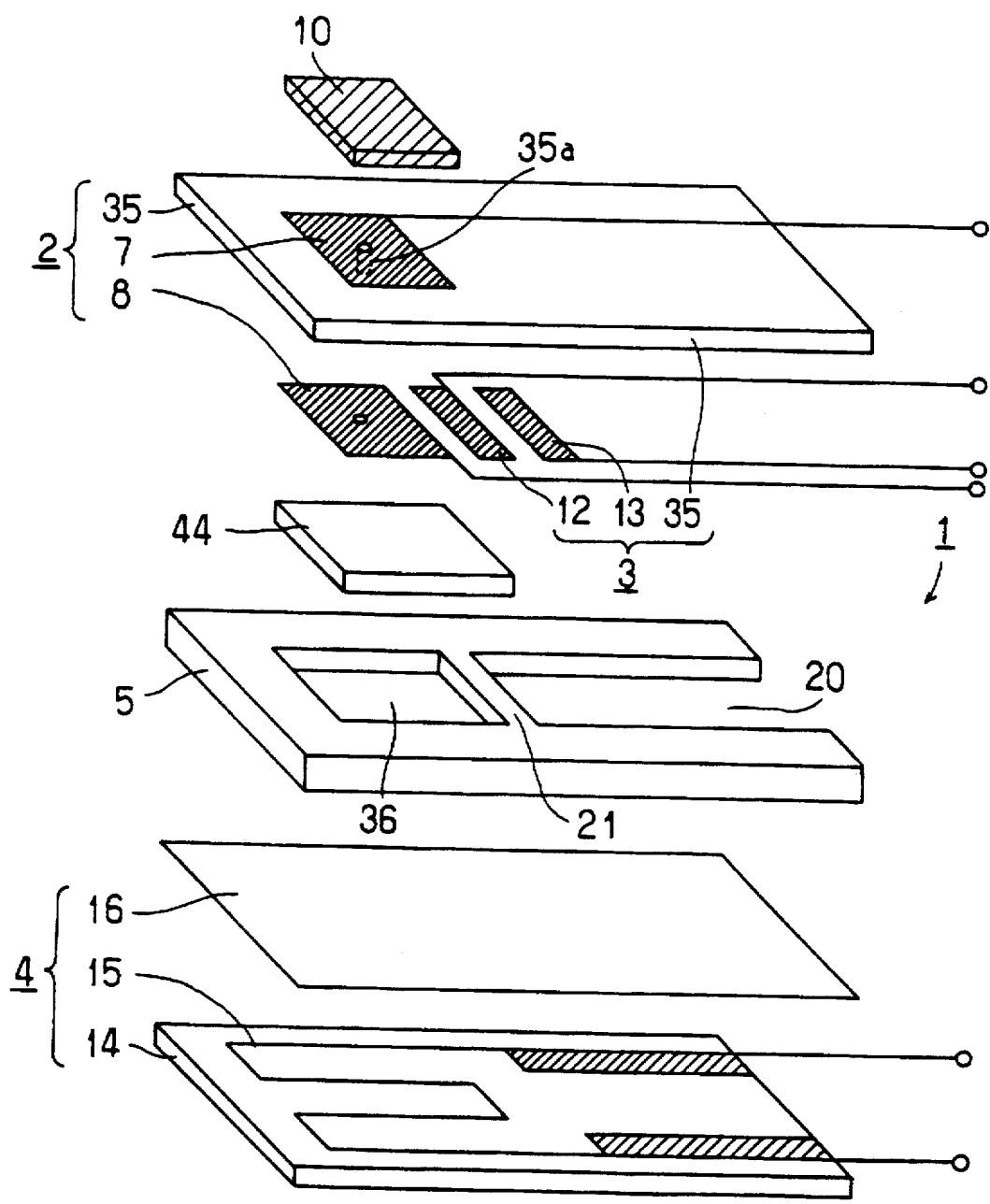
FIG. 5 is a schematic exploded view of the air-fuel ratio detecting element according to the second embodiment of the present invention.

As shown in FIG. 4 and FIG. 5, the second embodiment is substantially identical to the first embodiment except that the volume of the inner space 17 of the oxygen pump portion 2 is reduced by using a volume adjusting member 44. The volume adjusting member 44 is of a flat sheet which is made of the same material as that of the spacer 5, i.e. electrical insulating ceramic material such as alumina. The volume adjusting member 44 is fixed on the substrate 16 of the heating element 4, which functions as an insulating sheet, at a portion corresponding to the inner space 17.

As seen from FIG. 5, the volume adjusting member 44 has substantially the same size as the opening 36, and its thickness is thinner than the spacer 5 by 10 to 200 µm. Accordingly, when the spacer 5 is disposed on the heating element 4 and then when the volume adjusting member 44 is fit into the opening 36 of the spacer 5, the inner space 17 having a height of 10 to 200 µm is defined in the opening 36.

Other portions are identical to those of the first embodiment, and hence the description thereof is omitted.

The effects of the second embodiment will now be described.

As a result of fitting the volume adjusting member 44 into the opening 36 in the spacer 5, the volume of the inner space 17 of the oxygen pump portion 3 into which gas to be measured is led becomes smaller than that of the structure according to the first embodiment. That is, the volume of the inner space 17 of the oxygen pump portion 2 can be reduced without making it difficult to manufacture and handle the spacer 5 as in the case where the spacer 5 itself is made thinner. Also, the time required for the oxygen pump portion 2 to take in and out gas to be measured can be reduced, whereby the response of the air-fuel ratio detecting element 1 can be improved.

Also, as in the first embodiment, the number of solid electrolyte sheets 35 can be reduced, whereby the heating efficiency of the heating element 4 can be improved.

Third embodiment:

An air-fuel ratio detecting element according to a third embodiment of the present invention will now be described with reference to FIG. 6 and FIG. 7. In the air-fuel ratio detecting element of the present embodiment, a formed insert capable of reducing the inner space of an oxygen pump portion is used as volume adjusting means and in place of a spacer.

Figure 6:
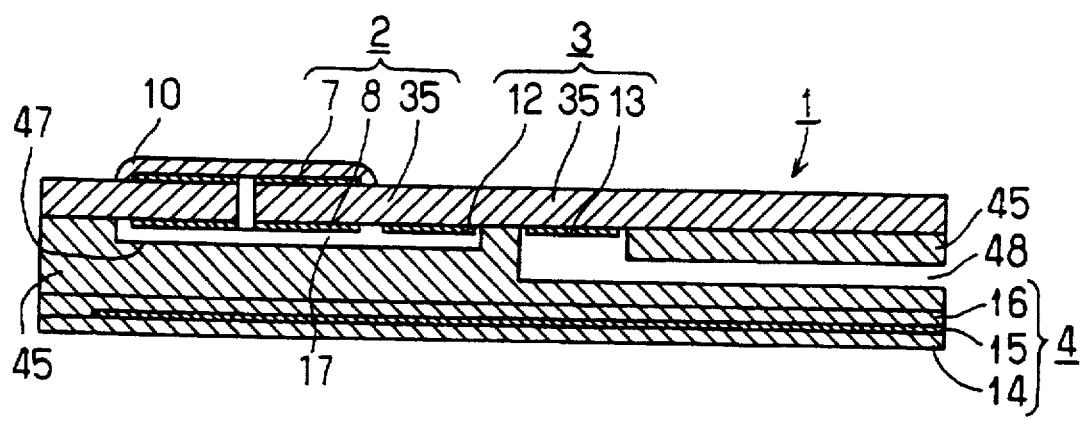
FIG. 6 is a schematic cross-sectional view of an air-fuel ratio detecting element according to a third embodiment of the present invention.
Figure 7:
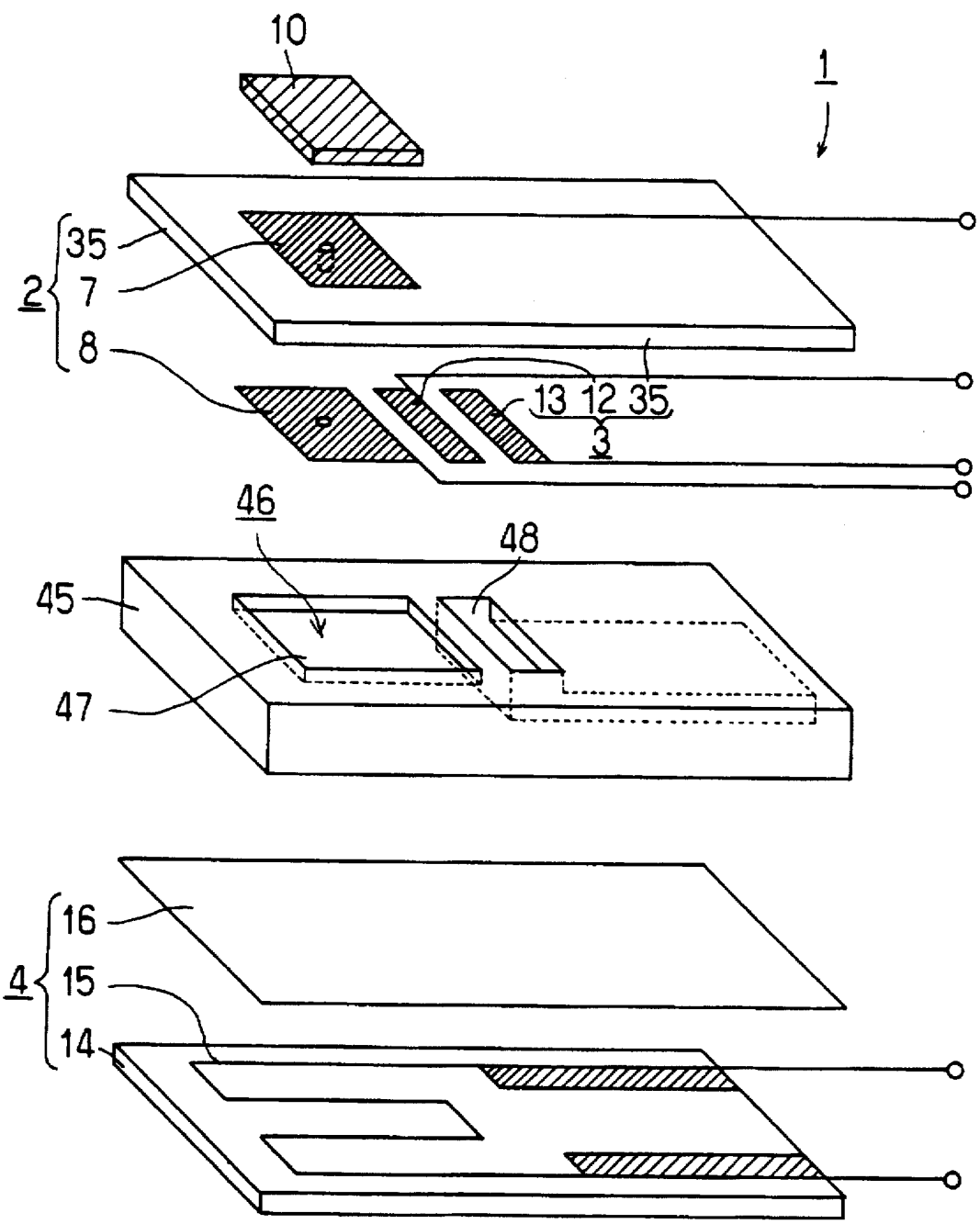
FIG. 7 is a schematic exploded view of the air-fuel ratio detecting element according to the third embodiment of the present invention.

As shown in FIG. 6 and FIG. 7, a formed insert 45 is basically a rectangular parallelepiped and made of a ceramic insulating material such as alumina. An open cavity 46 having a bottom 47 which is 10 to 200 mm deep is formed in the formed insert 45 at a portion which faces the electrode 8 of the oxygen pump portion 2 and the electrode 12 of the oxygen sensor portion 3. As shown in FIG. 6, an air passage 48 having an L-shaped cross section is formed through the formed insert 45. The air passage 48 penetrates from a portion facing the electrode 13 of the oxygen sensor portion 3 to the rear end which is opposite to the end where the open cavity 46 is provided. Thus constructed formed insert 45 is formed by injection molding or the like. Other portions are identical to those of the first embodiment, and hence the description thereof is omitted.

The effects of the third embodiment will now be described.

The open cavity 46 having the bottom 47 is formed in the formed insert 45 which functions as a spacer, whereby the inner space 17 of the oxygen pump portion 2 can be reduced to obtain the same effect as in the second embodiment. In addition, the structure becomes more simple than the second embodiment which is provided with the volume adjusting member 44 as a separate component.

Fourth embodiment:

An air-fuel ratio detecting element according to a third embodiment of the present invention will now be described with reference to FIG. 8 and FIG. 9. In the air-fuel ratio detecting element of the present embodiment, a heating element is provided on both sides of the oxygen pump portion 2 and the oxygen sensor portion 3.

Figure 8:
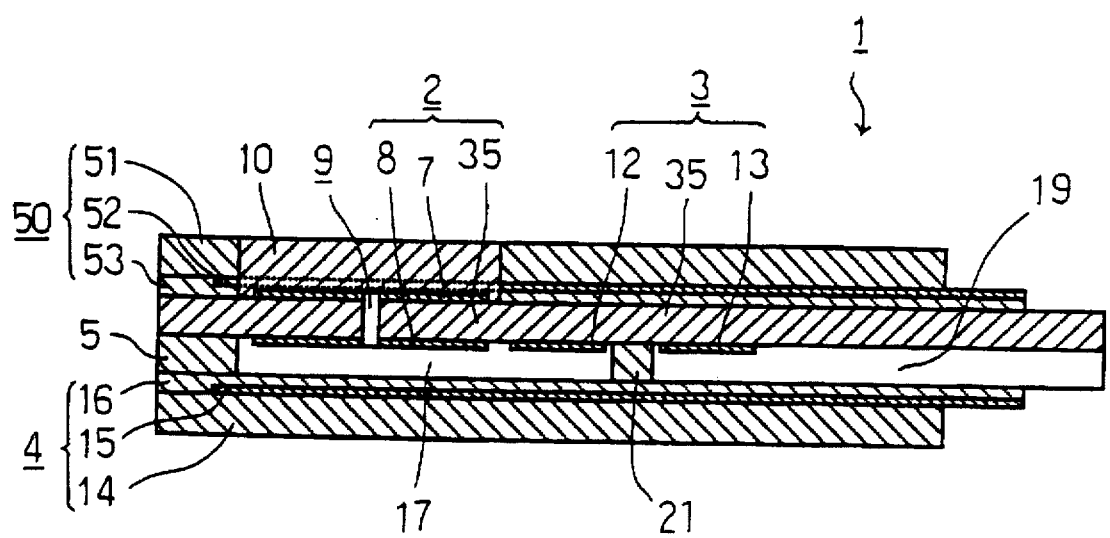
FIG. 8 is a schematic cross-sectional view of an air-fuel ratio detecting element according to a fourth embodiment of the present invention.
Figure 9:
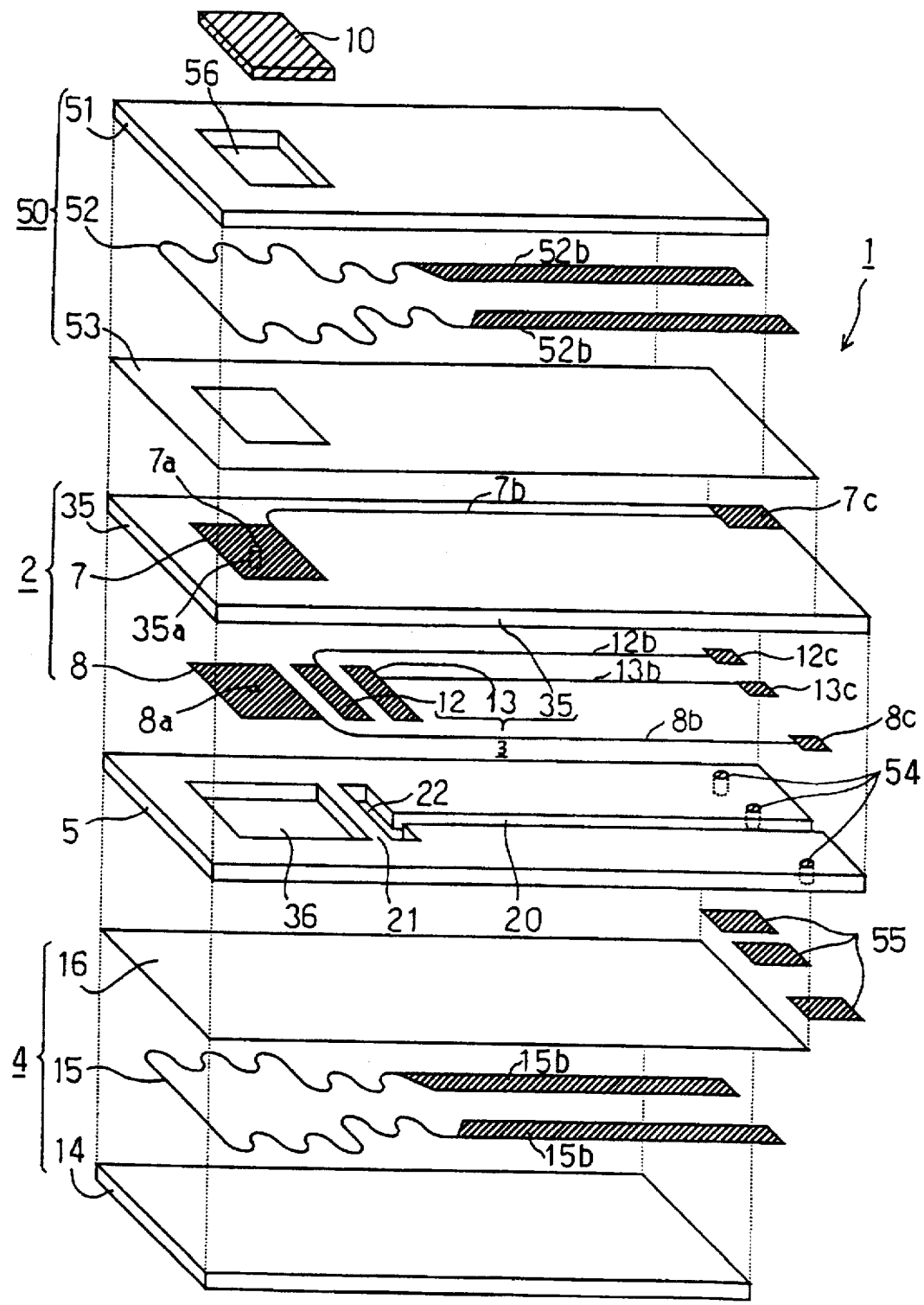
FIG. 9 is a schematic exploded view of the air-fuel ratio detecting element according to the fourth embodiment of the present invention.

As shown in FIG. 8 and FIG. 9, the fourth embodiment is the same as the first embodiment except that another heating element 50 is provided on the side of the solid electrolyte sheet 35, which side is exposed to gas to be measured.

The heating element 50 is composed of a substrate 51 made of an electrical insulating material such as alumina, a substrate 53 which is made of an electrical insulating material such as alumina and disposed so as to face the substrate 51, an electrical heating member 52 which is disposed between the substrates 51 and 53 and made of an electrical resisting material such as platinum, and leads 52b which are connected to the electrical heating member 52 and made of the same material as the electrical heating member 52.

In the fourth embodiment, the substrates 16 and 53 of the heating elements 4 and 5 have the same length but are longer than the substrates 14 and 51. Because of this difference in length, leads 15b of the heating element 4 and the leads 52b of the heating element 50 are exposed at the end portions of the substrates 16 and 53, respectively. This facilitates external connections of the leads 15b, 52b.

The solid electrolyte sheet 35 and the spacer 5 have the same length and are longer than the heating elements 4, 50, as shown in FIG. 9.

A lead 7b of the electrode 7 of the oxygen pump portion 2 is formed on the second side of the solid electrolyte sheet 35 along one side edge thereof and connected to a terminal 7c which is formed on the solid electrolyte sheet 35 at its corner.

A lead 8b of the electrode 8 of the oxygen pump portion 2 and leads 12b and 13b of the electrodes 12 and 13 of the oxygen sensor portion 3 are formed on the first side of the solid electrolyte sheet 35. The lead 8b runs along one side edge of the solid electrolyte sheet 35, the lead 12b runs along the other side edge of the solid electrolyte sheet 35, and the lead 13b runs near the centerline of the solid electrolyte sheet 35. These leads 8b, 12b, and 13b are connected to terminals 8c, 12c, and 13c which are formed on the solid electrolyte sheet 35 at an end portion, 8c and 12c being positioned at corners and 13c being positioned substantially at center.

Three through-holes 54 are formed in the end portion of the spacer 5 at positions corresponding to the terminals 8c, 12c, 13c. The spacer 5 is provided with terminals 55 which are formed on the side opposite to the side having the terminals 8c, 12c, 13c such that the terminals 55 are located at positions corresponding to the three through-holes 54. The terminals 8c, 12c, and 13c of the leads 8b, 12b, and 13b are connected to the three terminals 55 through conductive paint filled in the through-holes 54.

The opening 20 formed in the spacer 5 is narrower than that in the first embodiment and has a slit-like shape. An opening 22 which is integrally formed with the opening 20 is in a rectangular shape which has substantially the same dimensions as the electrode 13.

An opening 56 is formed in the substrate 51 of the heating element 50 at a portion which faces the electrode 7 of the oxygen pump portion 2, whereby the electrode 7 is exposed to gas to be measured. Since the electrode 7 is exposed through the opening 56, the porous ceramic protector 10 is fit into the opening 56 to cover the electrode 7.

The above-described terminals are of the same material as the leads, and the conductive paint filled in the through-holes 54 is also of the same material as the leads.

The effects of the fourth embodiment will now be described.

In the fourth embodiment, the heating elements 4, 50 are disposed on opposite sides of the solid electrolyte sheet 35, whereby the solid electrolyte sheet 35 can be heated from both sides. Accordingly, the heating capability is higher than the case where the heating element 4 is disposed only on one side as in the first embodiment. As a result, the temperature distribution can be made flatter across the thickness of the solid electrolyte sheet 35, whereby the solid electrolyte sheet 35 can be heated more efficiently. This reduces an electrical load imposed on the heating elements 4, 50, and thus a deterioration such as the breaking of wire is less likely to occur.

Even though a plurality of sheets are stacked, the leads of the heating elements 4, 50, the oxygen pump portion 2, and the oxygen sensor portion 3 are adequately arranged and combined with the through-holes 54 and the terminals 7c, 8c, 12, 13c, whereby the leads can be securely led out for external connections.

Furthermore, the openings 20, 22 for forming the air passage 19 occupy a smaller area, whereby the bonding area between the spacer 5 and the solid electrolyte sheet 35 and between the spacer 5 and the substrate 16 of the heating element 4 can be increased. As a result, separation between sheets can be avoided effectively.

Fifth embodiment:

An air-fuel ratio detecting element according to a fifth embodiment of the present invention will now be described with reference to FIG. 10 and FIG. 11. In the air-fuel ratio detecting element of the present embodiment, the oxygen pump portion 2 and the oxygen sensor portion 3 are formed on the same solid electrolyte sheet 35, and a slit is formed in the solid electrolyte sheet 35 across its width between the oxygen pump portion 2 and the oxygen sensor portion 3 for suppressing a current leak therebetween.

Figure 10:
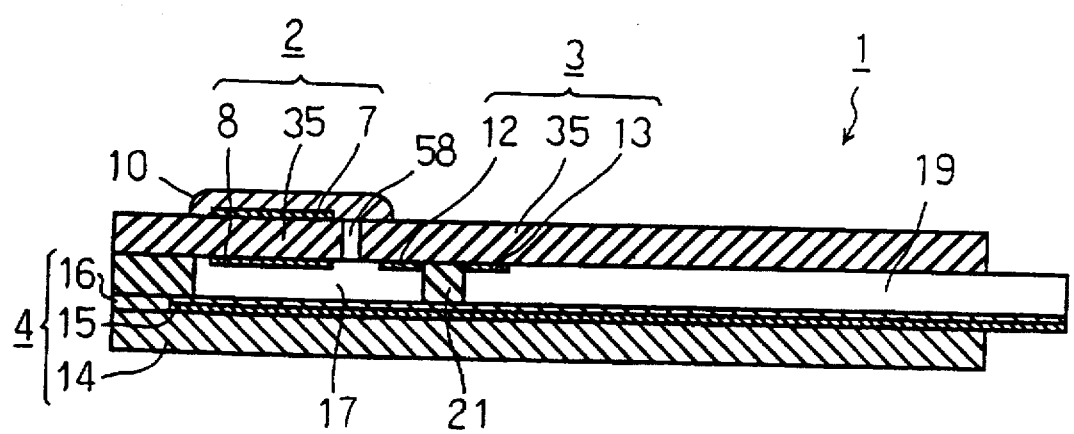
FIG. 10 is a schematic cross-sectional view of an air-fuel ratio detecting element according to a fifth embodiment of the present invention.
Figure 11:
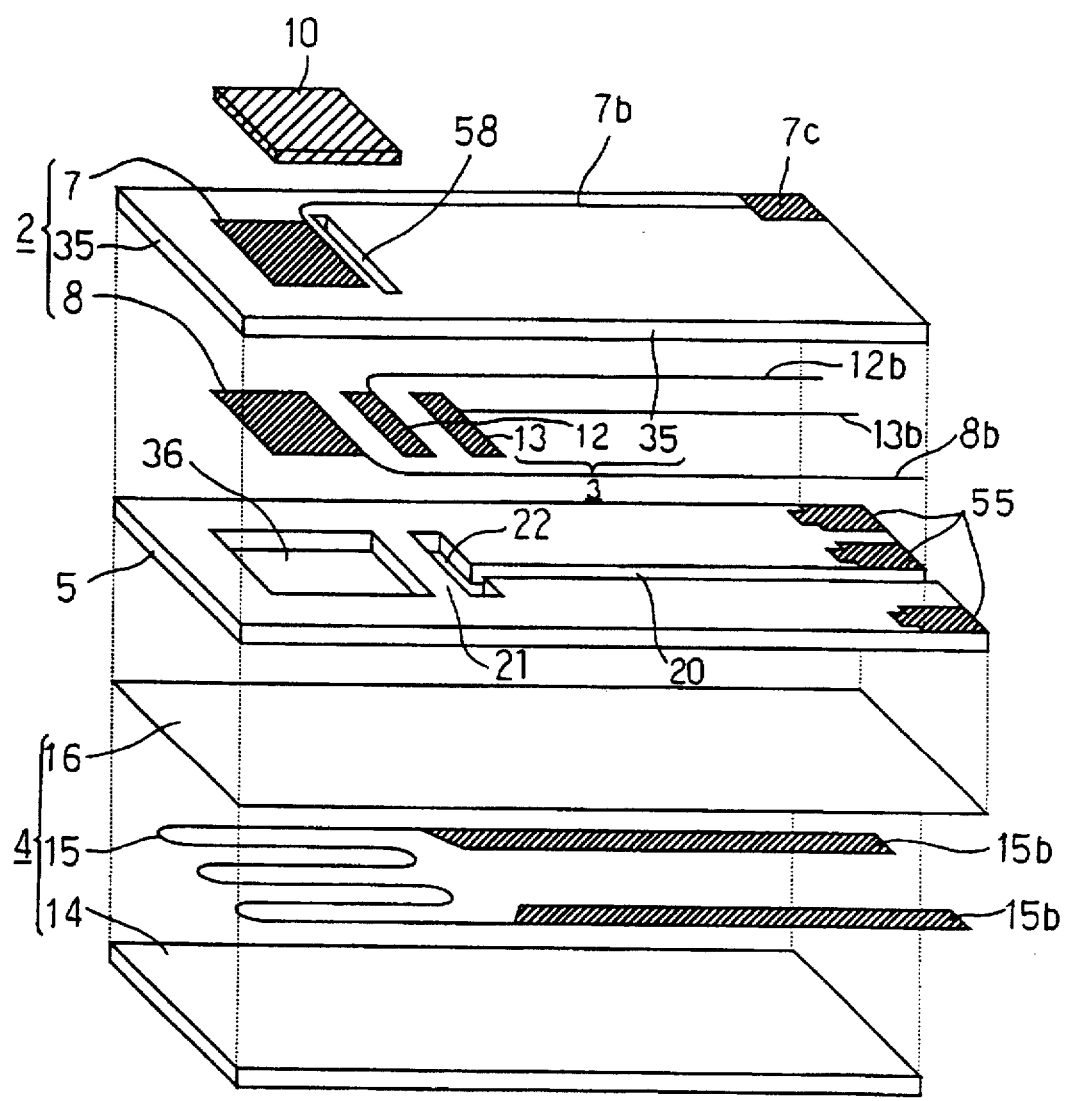
FIG. 11 is a schematic exploded view of the air-fuel ratio detecting element according to the fifth embodiment of the present invention.

As shown in FIG. 10 and FIG. 11, a slit 58 which is shorter than the width of the solid electrolyte sheet 35 is formed in the solid electrolyte sheet 35 across the width thereof such that the slit 58 is located between the oxygen pump portion 2 and the oxygen sensor portion 3.

The slit 58 is formed through the solid electrolyte sheet 35 in the direction of thickness thereof and positioned between the electrodes 7, 8 of the oxygen pump portion 2 and the electrode 12 of the oxygen sensor portion 3. As shown in FIG. 11, the length of the slit 58 in the widthwise direction of the solid electrolyte sheet 35 is longer than the length of the electrodes 8, 12 in the widthwise direction of the solid electrolyte sheet 35.

The electrode 8 of the oxygen pump portion 2 and the electrodes 12, 13 of the oxygen sensor portion 3 are connected through corresponding leads 8b, 12b, 13b to the terminals 55 which are formed on the end portion of the spacer 5. The spacer 5 is longer than the substrate 14 of the heating element 4 and the solid electrolyte sheet 35, whereby the terminals 55 can be provided for external connections.

The substrate 16 of the heating element 4 has the same length as that of the spacer 5 but longer than the substrate 14, so that the leads 15b of the heating member 15 disposed between the substrate 14 and the substrate 16 are exposed, whereby the leads 15b become connectable. The electrode 7 of the oxygen pump portion 2 is connected to the terminal 7c which is formed on the solid electrolyte sheet 35 at an end corner. The ceramic protector 10 is formed on the solid electrolyte sheet 35 so as to cover the slit 58 together with the electrode 7.

The effects of the fifth embodiment will now be described.

When the oxygen pump portion 2 and the oxygen sensor portion 3 share the same solid electrolyte sheet 35, a leak current may flow between the oxygen pump portion 2 and the oxygen sensor portion 3 depending on the structure of an electric circuit which processes signals received from the portions 2, 3.

According to the fifth embodiment, the slit 58 formed in the solid electrolyte sheet 35 functions to improve the electrical insulating performance between the oxygen pump portion 2 and the oxygen sensor portion 3, thereby preventing a leak current from flowing therebetween. As a result, a problem described below can be avoided.

The oxygen pump portion 2 takes oxygen into and out from the inner space 17 so that the oxygen sensor portion 3 outputs an output voltage corresponding to an excess air ratio ($\lambda$) of 1 which allows temperature dependency to be ignored. However, for example, if a leak current flows between the oxygen pump portion 2 and the oxygen sensor portion 3, the control is performed such that the air-fuel ratio becomes a value which deviates from the ratio ($\lambda$) of 1 and which corresponds to the control voltage. Furthermore, temperature dependency becomes unignorable, causing a further deterioration in performance of combustion. According to the fifth embodiment, the slit 58 is formed between the oxygen pump portion 2 and the oxygen sensor portion 3, whereby a leak current can be securely prevented from flowing between the oxygen pump portion 2 and the oxygen sensor portion 3. Thus, the problem described above can be avoided.

The slit 58 may be filled with a ceramic insulating material such as alumina for improving the strength of the periphery thereof. In this case, for example, a communication hole may be formed in the spacer 5 to take gas to be measured into the inner space 17.

Sixth embodiment:

An air-fuel ratio detecting element according to a sixth embodiment of the present invention will now be described with reference to FIG. 12 and FIG. 13. In the air-fuel ratio detecting element of the present embodiment, the oxygen pump portion 2 and the oxygen sensor portion 3 are formed on the same solid electrolyte sheet 35, and the air passage 19 is formed on the side of the solid electrolyte sheet 35, which side is opposite to the side facing the inner space 17.

Figure 12:
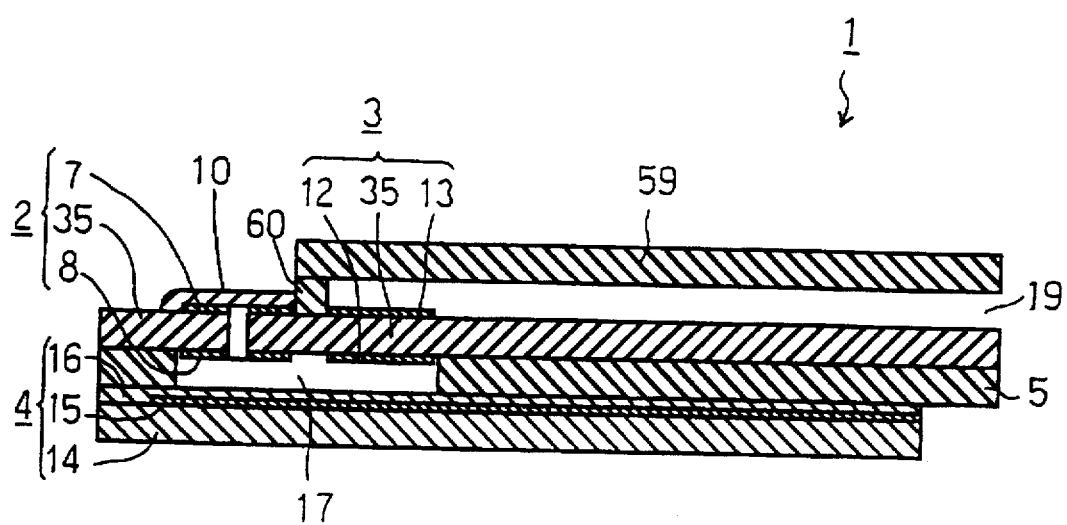
FIG. 12 is a schematic cross-sectional view of an air-fuel ratio detecting element according to a sixth embodiment of the present invention.
Figure 13:
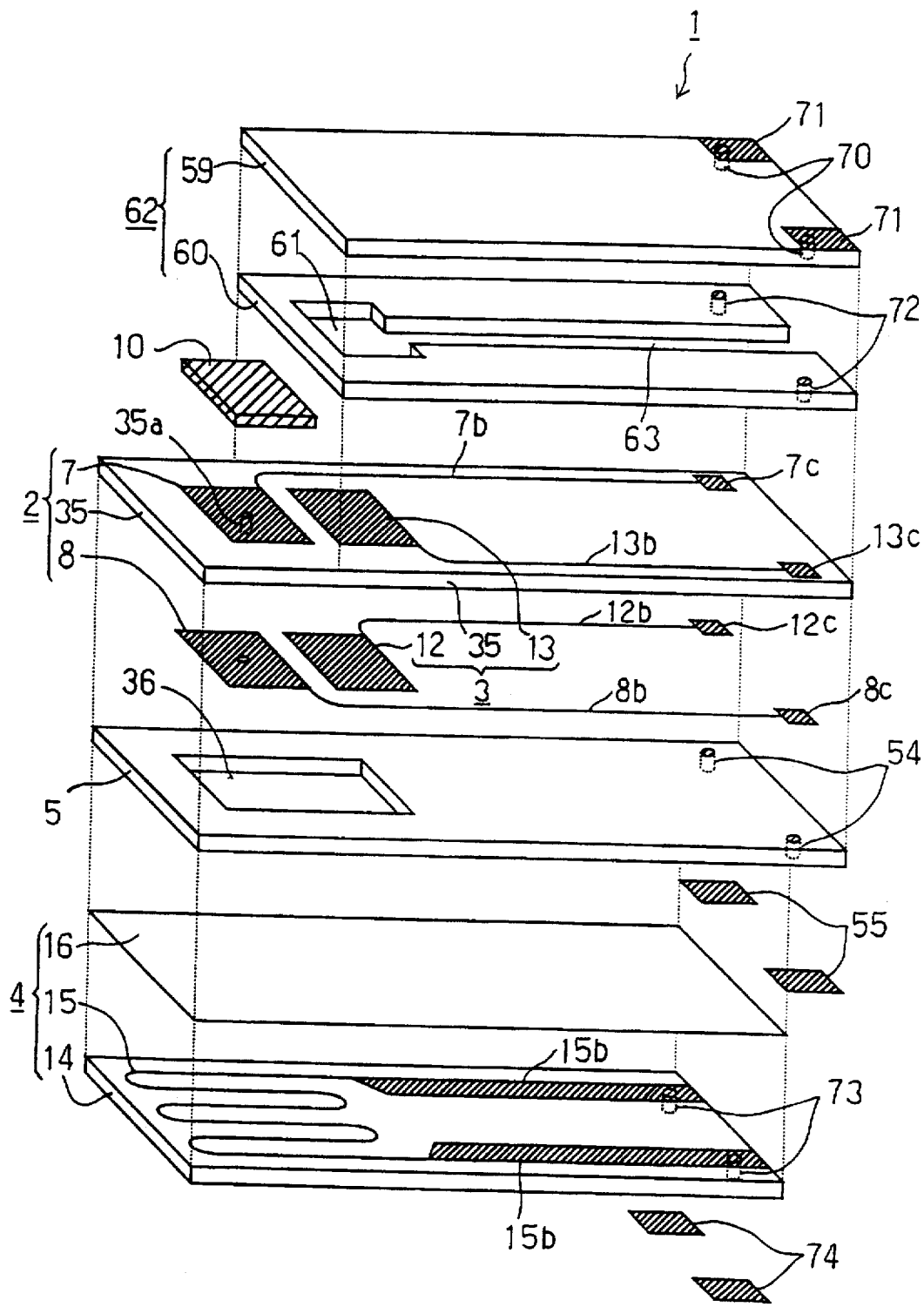
FIG. 13 is a schematic exploded view of the air-fuel ratio detecting element according to the sixth embodiment of the present invention.

In the sixth embodiment shown in FIG. 12 and FIG. 13, the electrodes 12 and 13 are formed on opposite sides of the solid electrolyte sheet 35 to form the oxygen sensor portion 3, while in the first through fifth embodiments, a pair of electrodes is formed on the same side of the solid electrolyte sheet 35 to form the oxygen sensor portion 3.

Because of thus constructed oxygen sensor portion 3, the air passage 19 is positioned opposite to the inner space 17 with respect to the solid electrolyte sheet 35.

In detail, an air passage forming portion 62 which is composed of a spacer 60 made of a ceramic insulating material such as alumina and a substrate 59 made of a ceramic insulating material such as alumina is disposed on the solid electrolyte sheet 35. The spacer 60 has an opening 61 at a portion which faces the electrode 13 when disposed on the solid electrolyte sheet 35 and an opening 63 which extends along its centerline to its rear end. The opening 61 functions to expose the electrode 13 to the air, and the opening 63 functions to define the air passage 19.

As shown in FIG. 13, the spacer 5 has an opening 36 at its forward end portion which faces the electrodes 8, 12 to define a space between the solid electrolyte sheet 35 and the substrate 16 of the heating element 4.

The rear end of the substrate 59, the rear end of the solid electrolyte sheet 35, and the rear end of the spacer 5 are aligned (at right in FIG. 13). The electrodes 7, 13 formed on the same side of the solid electrolyte sheet 35 are connected through the leads 7b, 13b to the terminals 7c, 13c, respectively, which are formed on the solid electrolyte sheet 35 at its rear corners. Through-holes 70 are formed in the substrate 59 at its rear corners, and terminals 71 are formed at the same corners. Also, through-holes 72 are formed in the spacer 60 at its rear corners such that the through-holes 72 are situated on both sides of the opening 63. The terminals 7c, 13c are connected to the terminals 71 through conductive paint filled in the through-holes 70, 72.

On the other hand, the through-holes 54 are formed in the spacer 5 at its rear corners. The terminals 8c, 12c of the electrode 8 of the oxygen pump portion 2 and the electrode 12 of the oxygen sensor portion 3 are positioned in correspondence with the through-holes 54. The terminals 55 are formed on the back side of the spacer 5 such that the terminals 55 are situated at positions corresponding to the through-holes 54. The terminals 8c, 12c are connected to the terminals 55 through conductive paint filled in the through-holes 54. Through-holes 73 are formed in the substrate 16 of the heating element 4 at its rear end to be located at positions corresponding to the leads 15b of the heating member 15. Also, terminals 74 are formed on the back side of the substrate 16 such that the terminals 74 are situated at positions corresponding to the through-holes 73. The leads 15b are connected to the terminals 74 through conductive pain filled in the through-holes 73.

According to the sixth embodiment, the electrodes 12 and 13 of the oxygen sensor portion 3 are opposed to each other with respect to the solid electrolyte sheet 35 as in the case of the oxygen pump portion 2. Accordingly, compared with the case where the electrodes 12, 13 of the oxygen sensor portion 3 are arranged side by side, an increase in the length of the solid electrolyte sheet 35 associated with an increase in the area of an electrode can be avoided.

Seventh embodiment:

An air-fuel ratio detecting element according to a seventh embodiment of the present invention will be described with reference to FIG. 14 and FIG. 15. The present embodiment is a modification of the sixth embodiment.

Figure 14:
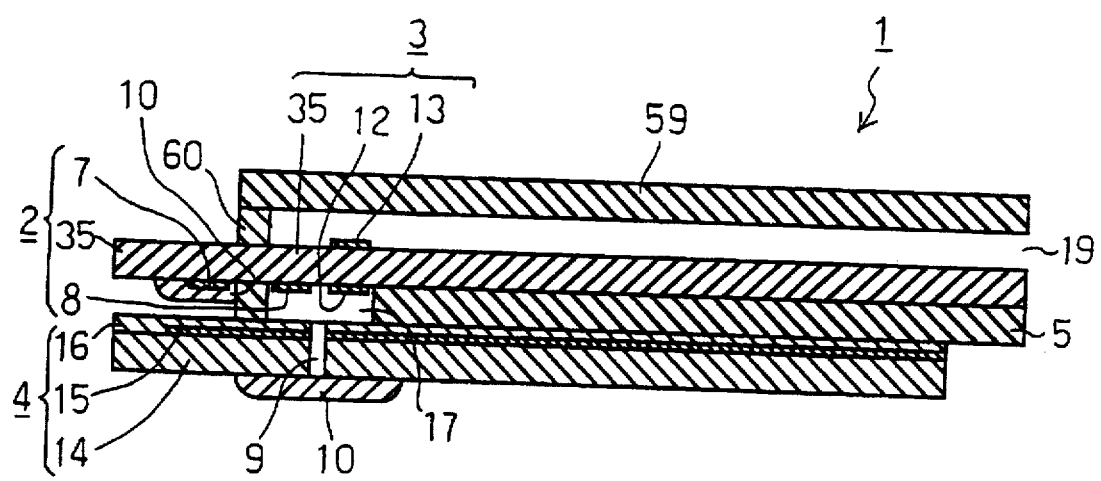
FIG. 14 is a schematic cross-sectional view of an air-fuel ratio detecting element according to a seventh embodiment of the present invention.
Figure 15:
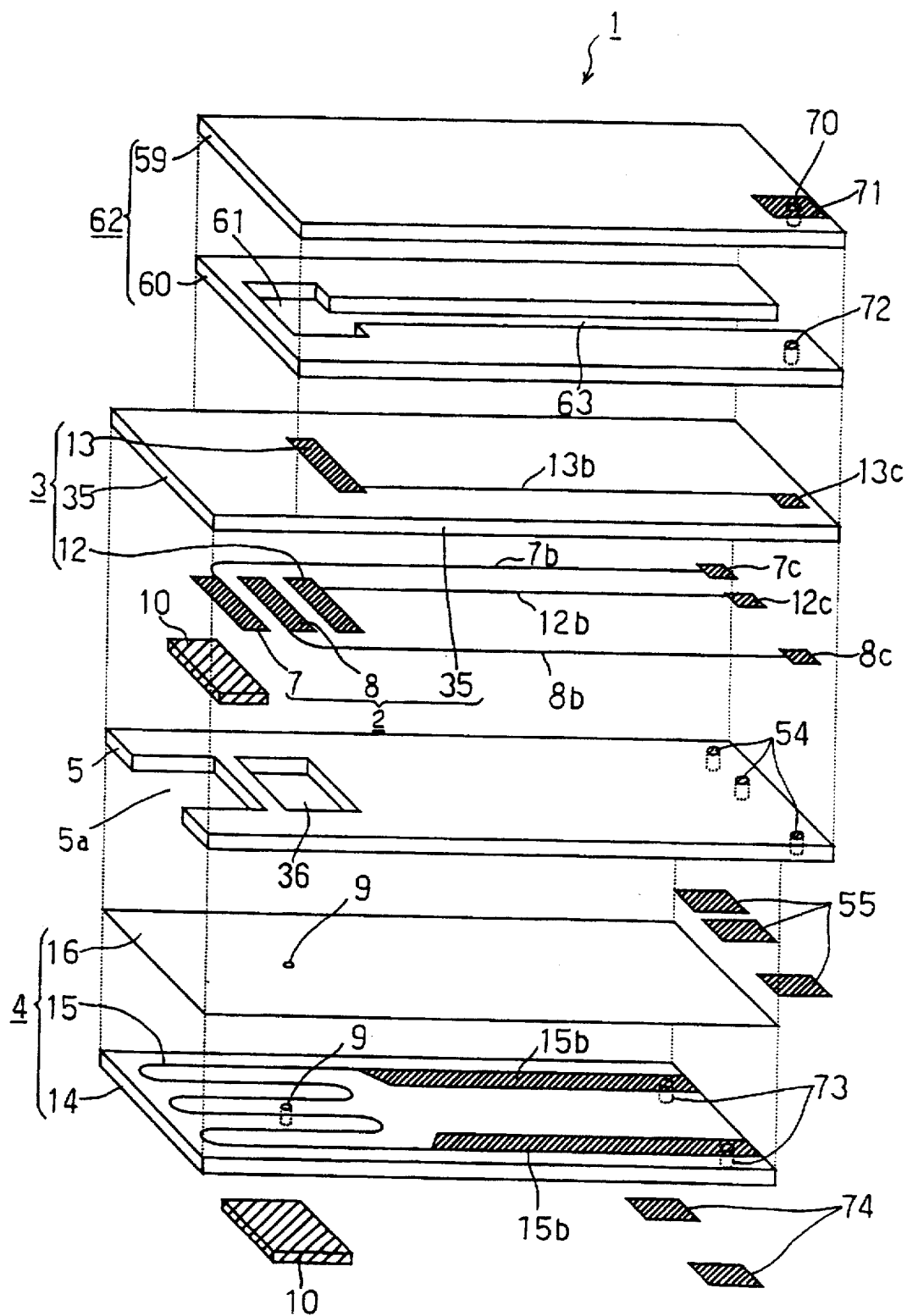
FIG. 15 is a schematic exploded view of the air-fuel ratio detecting element according to the seventh embodiment of the present invention.

As shown in FIG. 14 and FIG. 15, a separate substrate 59 and a spacer 60 are used to form the air passage 19, as in the sixth embodiment. In the sixth embodiment, the electrodes 7, 8 of the oxygen pump portion 2 are formed on opposite sides of the solid electrolyte sheet 35, whereas in the seventh embodiment, the electrodes 7, 8 are formed on the same side of the solid electrolyte sheet 35.

As shown in FIGS. 14 and 15, to expose the electrode 7 of the oxygen pump portion 2 to gas to be measured, the spacer 5 has a cut-away portion 5a at its forward end.

Also, in the seventh embodiment, the communication hole 9 is formed in the substrates 14, 16 of the heating element 4 to lead gas to be measured into the inner space 17. The porous ceramic protector 10 is also provided on the substrate 14 of the heating element 4 at the open end of the communication hole 9.

The electrodes 7, 8, 12, 13 of the oxygen pump portion 2 and the oxygen sensor portion 3 are led out for external connections by combining through-holes and terminals as in the sixth embodiment.

The effects of the seventh embodiment will now be described. In the seventh embodiment, the electrodes 7, 8 of the oxygen pump portion 2 are formed on the same side of the solid electrolyte sheet 35, the cut-away portion 5a is formed in the end portion of the spacer 5 for exposing the electrode 7 of the oxygen pump portion 2 to gas to be measured, and the communication hole 9 is formed in the heating element 4. Accordingly, compared with the sixth embodiment of FIG. 12, the forward end of the spacer 60 for defining the air passage 19 can be brought more closer to the forward end of the solid electrolyte sheet 35. This means that the length of the air-fuel ratio detecting element can be reduced.

Eighth embodiment:

An air-fuel ratio detecting element according to an eighth embodiment of the present invention will now be described with reference to FIG. 16 and FIG. 17. In the air-fuel ratio detecting element of the present embodiment, the oxygen pump portion 2 and the oxygen sensor portion 3 are formed on the same solid electrolyte sheet 35.

Figure 16:
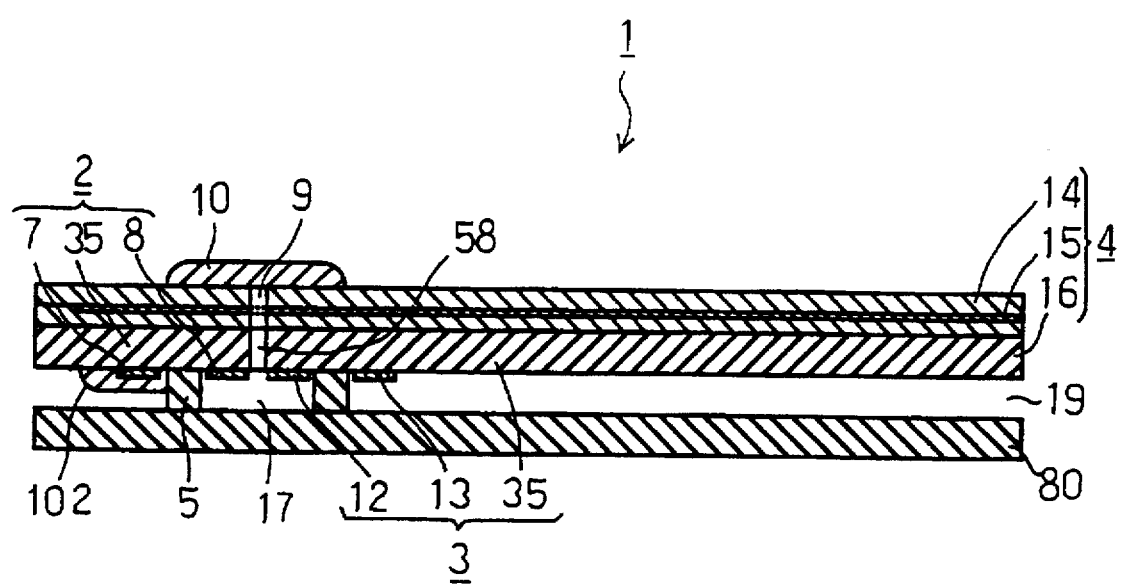
FIG. 16 is a schematic cross-sectional view of an air-fuel ratio detecting element according to an eighth embodiment of the present invention.
Figure 17:
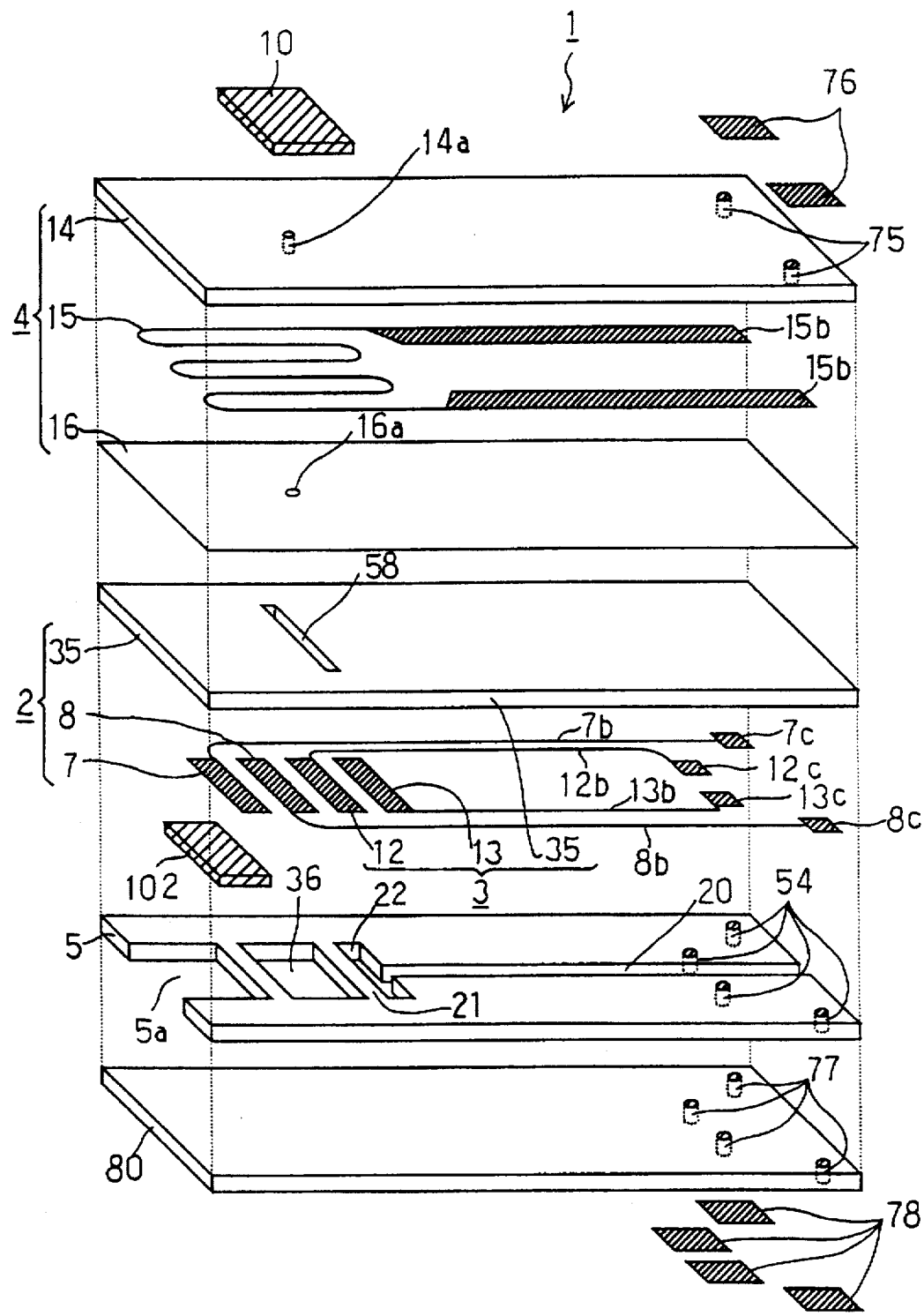
FIG. 17 is a schematic exploded view of the air-fuel ratio detecting element according to the eighth embodiment of the present invention.

In the eighth embodiment shown in FIG. 16 and FIG. 17, the electrodes 7, 8 of the oxygen pump portion 2 and the electrodes 12, 13 of the oxygen sensor portion 3 are formed on the same side of the solid electrolyte sheet 35. Also, the heating element 4 is directly disposed on the other side of the solid electrolyte sheet 35.

In detail, a substrate 80 made of a ceramic insulating material such as alumina is opposed to the solid electrolyte sheet 35 with the spacer 5 made of the same material as the substrate 80 being held therebetween. The heating element 4 is disposed on the side of the solid electrolyte sheet 35, which side is opposite to the side facing the substrate 80. The mutually separated electrodes 7, 8, 12, 13 are formed on the solid electrolyte sheet 35 on the same side as the substrate 80. The spacer 5 has a cut-away portion 5a for exposing the electrode 7 to gas to be measured, an opening 36 for defining the inner space 17 with the solid electrolyte sheet 35 and exposing the electrodes 8, 12 to thus defined inner space 17, and the openings 20, 22 for defining the air passage 19 and exposing the electrode 13 to thus defined air passage 19. Porous ceramic protector 102 surrounds electrode 7.

As in the fifth embodiment, the slit 58 preventing a leak current from flowing between the oxygen pump portion and the oxygen sensor portion 3 is formed in the solid electrolyte sheet 35 such that the slit 58 is situated between the electrodes 8 and 12 so as to isolate them from each other. Also, according to the eighth embodiment, to utilize the slit 58 as a hole for leading gas to be measured into the inner space 17, holes 14a and 16a are formed in the substrates 14 and 16 of the heating element 4 at a position corresponding to the slit 58. The holes 14a, 16a compose the communication hole 9.

Also, in the eighth embodiment as in other embodiments, the leads 7b, 8b of the electrodes 7, 8 of the oxygen pump portion 2 and the leads 12b, 13b of the electrodes 12, 13 of the oxygen sensor portion 3 are connected to terminals 78 using the through-holes 54 in the spacer 5 and through-holes 77 in the substrate 80. Also, the leads 15b of the heating element 4 are connected to terminals 76 using through-holes 75 in the substrate 14.

The effects of the eighth embodiment will now be described. A pair of electrodes 7, 8 of the oxygen pump portion 2 and a pair of electrodes 12, 13 of the oxygen sensor portion 3 are formed on the same side of the solid electrolyte sheet 35, and thus a beneficial effect in manufacture is produced. Also, since the electrodes can be formed on the solid electrolyte sheet 35 in one process, advantage in manufacture is produced. In addition, since the heating element 4 is directly disposed on the solid electrolyte sheet 35, heat generated by the heating element 4 directly acts on the solid electrolyte sheet 35, whereby the heating element 4 provides a quite good thermal efficiency.

Ninth embodiment:

An air-fuel ratio detecting element according to a ninth embodiment of the present invention will now be described with reference to FIG. 18 and FIG. 19. In the air-fuel ratio detecting element of the present embodiment, a heating element having an opening is disposed between the oxygen pump portion 2 and the oxygen sensor portion 3.

Figure 18:
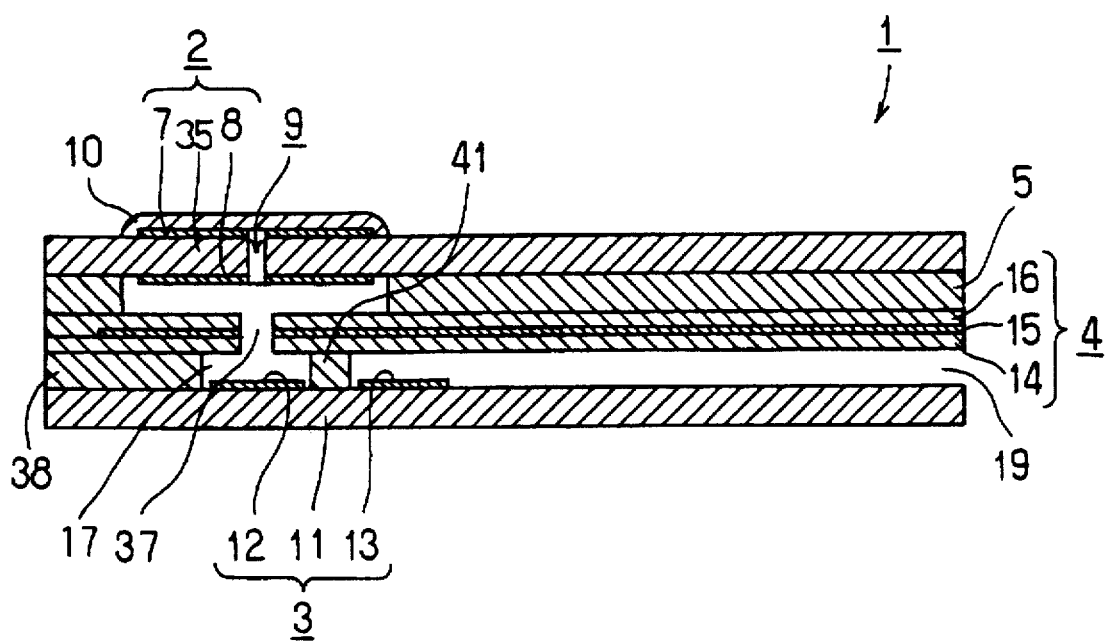
FIG. 18 is a schematic cross-sectional view of an air-fuel ratio detecting element according to a ninth embodiment of the present invention.
Figure 19:
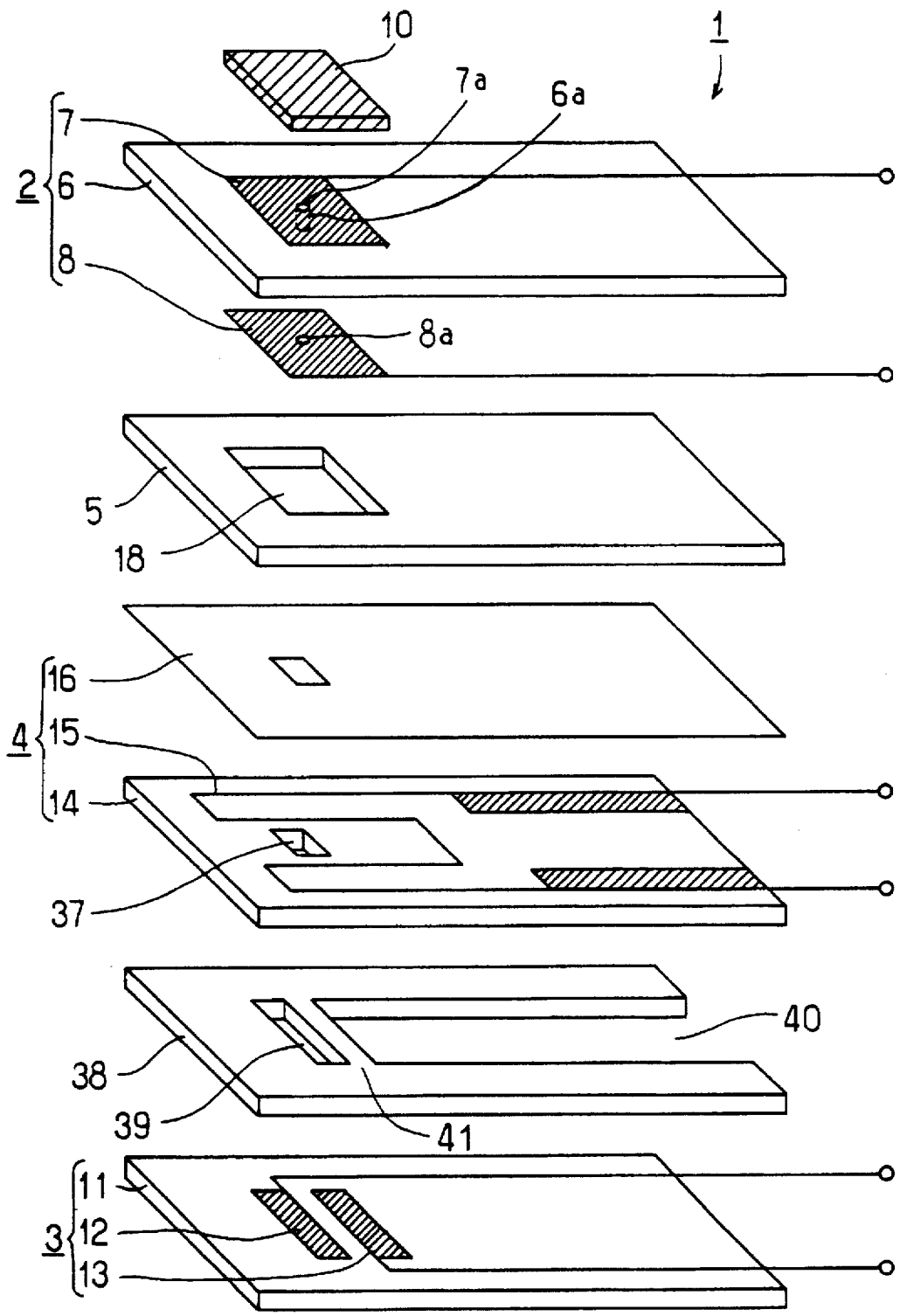
FIG. 19 is a schematic exploded view of the air-fuel ratio detecting element according to the ninth embodiment of the present invention.

In the ninth embodiment shown in FIG. 18 and FIG. 19, in addition to the solid electrolyte sheet 35 for the oxygen pump portion 2, a solid electrolyte sheet 11 is provided for the oxygen sensor portion 3, and the heating element 4 is disposed between the oxygen pump portion 2 and the oxygen sensor portion 3.

The spacer 5 made of a ceramic insulating material such as alumina has an opening 18 at a portion which faces the electrode 8, and the opening 18 becomes a part of the inner space 17. The opening 18 is substantially as large as the electrode 8. The spacer 38 has substantially the same shape as the spacer 5 of the first embodiment and has an opening 39 which becomes a part of the inner space 17 and an opening 40 which forms the air passage 19. The opening 39 is substantially as large as the electrode 12 of the oxygen sensor portion 3. The spacer 38 has a partition 41 which is located between the openings 39 and 40 and which serves as isolating means for isolating the inner space 17 from the air passage 19 when stacked. The heating element 4 has an opening 37 at a portion which faces the electrodes 8 and 12.

The spacer 5 is superposed on the oxygen pump portion 2 in such a manner that the opening 18 and the electrode 8 face each other. Furthermore, the heating element 4 is superposed on the spacer 5 in such a manner that the opening 37 and the opening 18 face each other. Also, the spacer 38 is superposed on the heating element 4 in such a manner that the opening 39 and the opening 37 face each other. Then, the oxygen sensor portion 3 is superposed on the spacer 38 in such a manner that the electrode 12 and the opening 39 face each other and that the electrode 13 and the opening 40 face each other. That is, in FIGS. 18 and 19, the oxygen pump portion 2, the spacer 5, the heating element 4, the spacer 38, and the oxygen sensor portion 3 are layered from top to bottom.

The inner space 17 is defined between the oxygen pump portion 2 and the oxygen sensor portion 3 by the oxygen pump portion 2, the openings 18, 39, and the oxygen sensor portion 3. The heating element 4 is disposed between the spacer 5 and the spacer 38 in such a manner that it divides the inner space 17. However, since the heating element 4 is disposed in such a manner that the opening 37 therein is located in the inner space 17, divided portions of the inner space 17 communicate with each other through the opening 37.

The effects of the ninth embodiment will now be described.

In the ninth embodiment, the oxygen sensor portion 3 and the oxygen pump portion 2 are disposed on opposite sides of the heating element 4 with the spacers 5, 38 held therebetween, respectively. Accordingly, by energizing the heating element 4, the temperature of the solid electrolyte sheet 35 of the oxygen pump portion 2 and the temperature of the solid electrolyte sheet 11 of the oxygen sensor portion 3 can be raised concurrently. Thus, the heating element 4 can transmit heat to the solid electrolyte sheets 35, 11 uniformly and efficiently.

The oxygen pump portion 2 takes oxygen into and out from the inner space 17 so that the oxygen sensor portion 3 shows an output voltage corresponding to an excess air ratio ($\lambda$) of 1 which allows temperature dependency to be ignored. However, for example, if electrical insulation is poor between the oxygen pump portion 2 and the heating element 4 or between the oxygen sensor portion 3 and the heating element 4, a leak current will flow from the heating element 4 to the oxygen pump portion 2 or the oxygen sensor portion 3. As a result, the air-fuel ratio is controlled to a value which deviates from the ratio ($\lambda$) of 1 which corresponds to the control voltage. Furthermore, temperature dependency becomes unignorable, causing a further deterioration in performance of combustion. However, according to the ninth embodiment, the spacers 5, 38 are of a ceramic insulating material such as alumina, and hence a leak current can be securely prevented from flowing from the heating element 4 to the oxygen pump portion 2 or the oxygen sensor portion 3. Thus, the above problem can be avoided. Also, of electrical insulating ceramic materials, alumina in particular does not undergo solution with zirconia, which is a material for the solid electrolyte sheets 35, 11. Hence, even when the spacers 5, 38 and the solid electrolyte sheets 35, 11 are baked together in manufacture, characteristics of the solid electrolyte sheets 35, 11 remain unchanged.

Structural features of the ninth embodiment will now be described.

The inner space 17 communicates with gas to be measured. In the oxygen pump portion 2, the electrodes 7 and 8 are provided on opposite sides of the solid electrolyte sheet 35. The electrode 8 is exposed to the inner space 17, and the electrode 7 is exposed to gas to be measured. In the oxygen sensor portion 3, the electrodes 12, 13 are provided on the same side of the solid electrolyte sheet 11. The electrode 12 is exposed to the inner space 17, and the electrode 13 is exposed to the opening 19 in which gas of a reference oxygen concentration exists and which is isolated from the inner space 17. The heating element 4 is disposed so as to heat the solid electrolyte sheet 35 of the oxygen pump portion 2 and the solid electrolyte sheet 11 of the oxygen sensor portion 3. Also, the heating element has the opening 37. At one end of the heating element 4 where the opening 37 is formed, the oxygen pump portion 2 is disposed on one side of the heating element 4 while the oxygen sensor portion 3 is disposed on the other side of the heating element 4. Thus, the inner space 17 is formed between the oxygen pump portion 2 and the oxygen sensor portion 3 with the opening 37 as an integral part thereof.

The effects of thus constructed ninth embodiment is as described above.

Tenth embodiment:

A control circuit which is used for the first through ninth embodiments will now be described with reference to FIG. 20.

Figure 20:
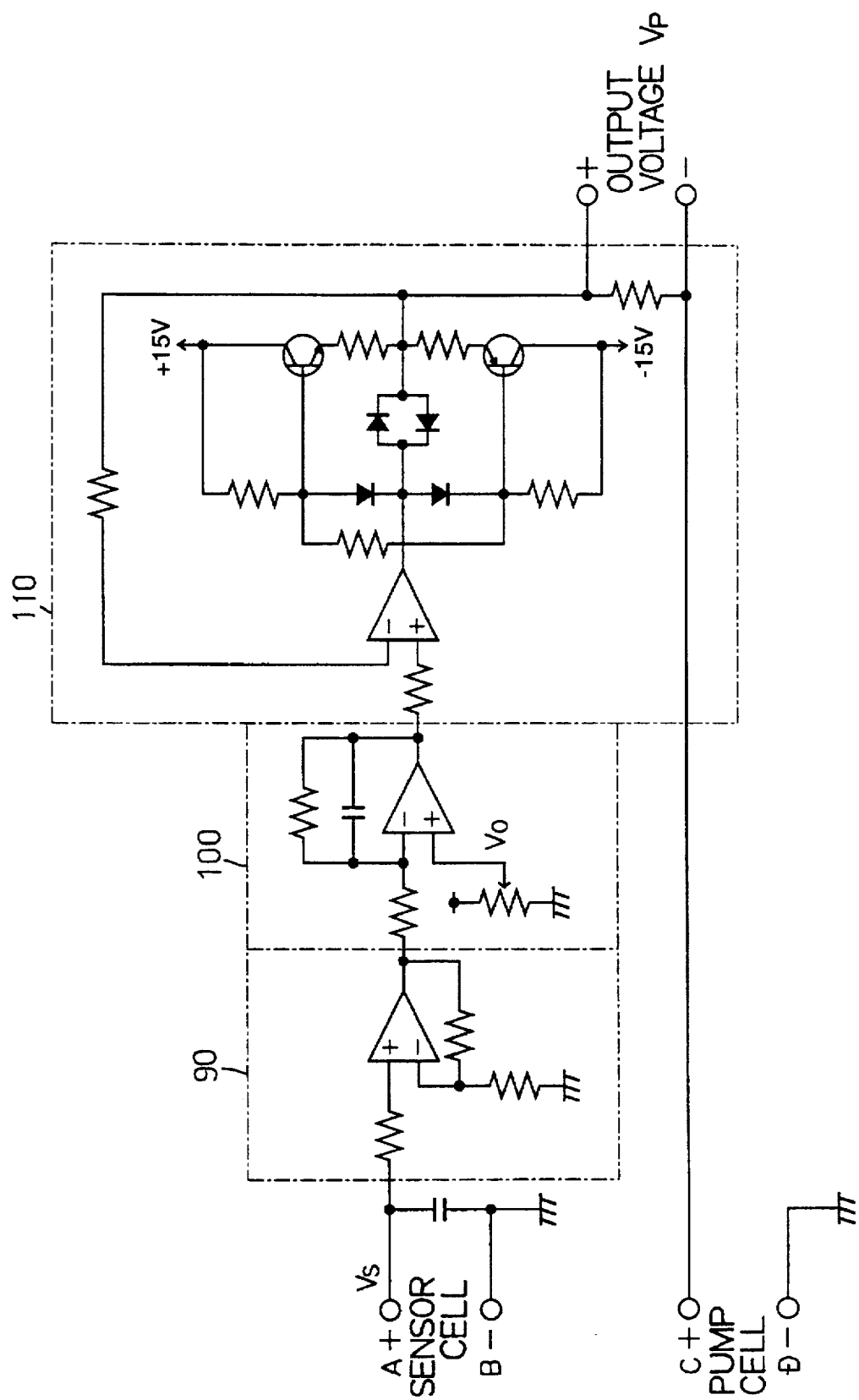
FIG. 20 is a diagram showing a control circuit which is used together with the air-fuel ratio detecting elements of the present invention.
Figure 21:
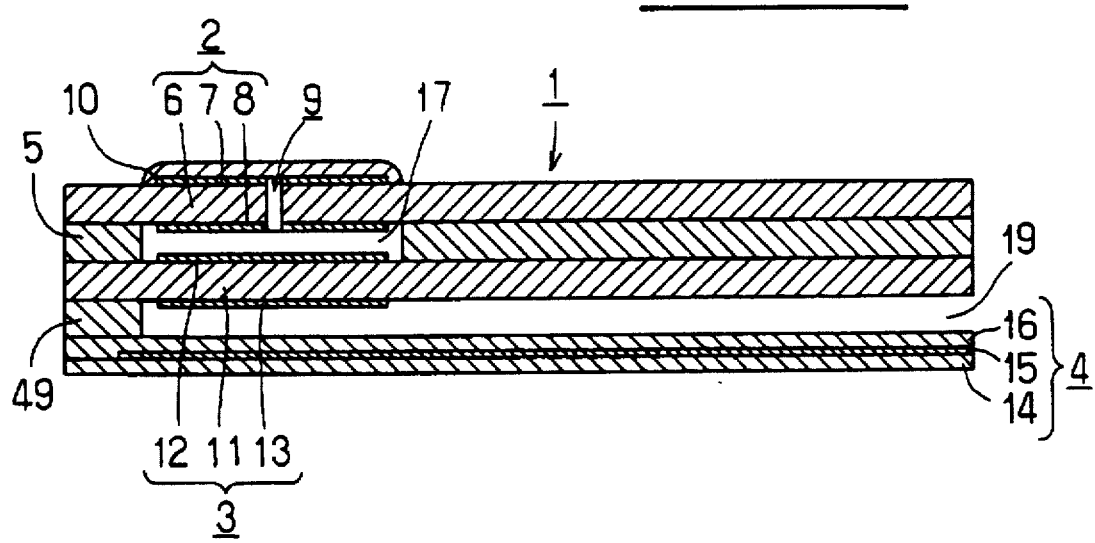
FIG. 21 is a schematic cross-sectional view of a conventional air-fuel ratio detecting element.

In FIG. 20, numeral 90 denotes a non-inverted amplifier circuit, numeral 100 denotes a comparison/control circuit, and numeral 110 denotes an output circuit. Characters A and B denote terminals to which the electrodes of the oxygen sensor portion 3 are connected. The electrode 13 (exposed to the air passage 19) of the oxygen sensor portion 3 is connected to terminal A. The electrode 12 (exposed to the inner space 17) of the oxygen sensor portion 3 is connected to terminal B. Characters C and D denote terminals to which the electrodes of the oxygen pump portion 2 are connected. The electrode 7 (exposed to gas to be measured) of the oxygen pump portion 2 is connected to terminal C. The electrode 8 (exposed to the inner space 17) of the oxygen pump portion 2 is connected to terminal D.

A sensor voltage which is produced between the electrodes 12 and 13 of the oxygen sensor portion 3, i.e. a sensor voltage Vs, which is generated based on the difference in oxygen concentration between the inner space 17 and the air passage 19, is inputted to the non-inverted amplifier circuit 90 and amplified thereby.

The comparison/control circuit 100 compares the sensor voltage with a preset voltage Vo, and outputs a control voltage corresponding to the difference between them. The outputted control voltage is applied via an output circuit 110 to the electrodes 7 and 8 of the oxygen pump portion 2. The output circuit 110 outputs a signal Vp which represents the current flowing through the oxygen pump portion 2.

The output signal Vp corresponds to the concentration of oxygen in gas to be measured. Thus, by monitoring the output signal Vp, the air-fuel ratio of gas to be measured is obtained.

Figure 22:
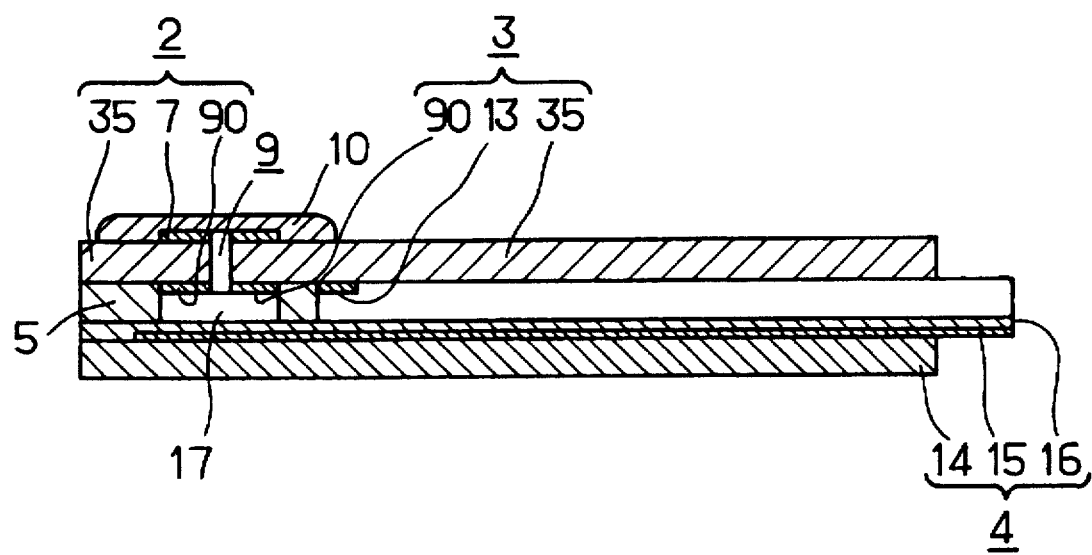
FIG. 22 is a schematic cross-sectional view of an air-fuel ratio detecting element according to an eleventh embodiment of the present invention.
Figure 23:
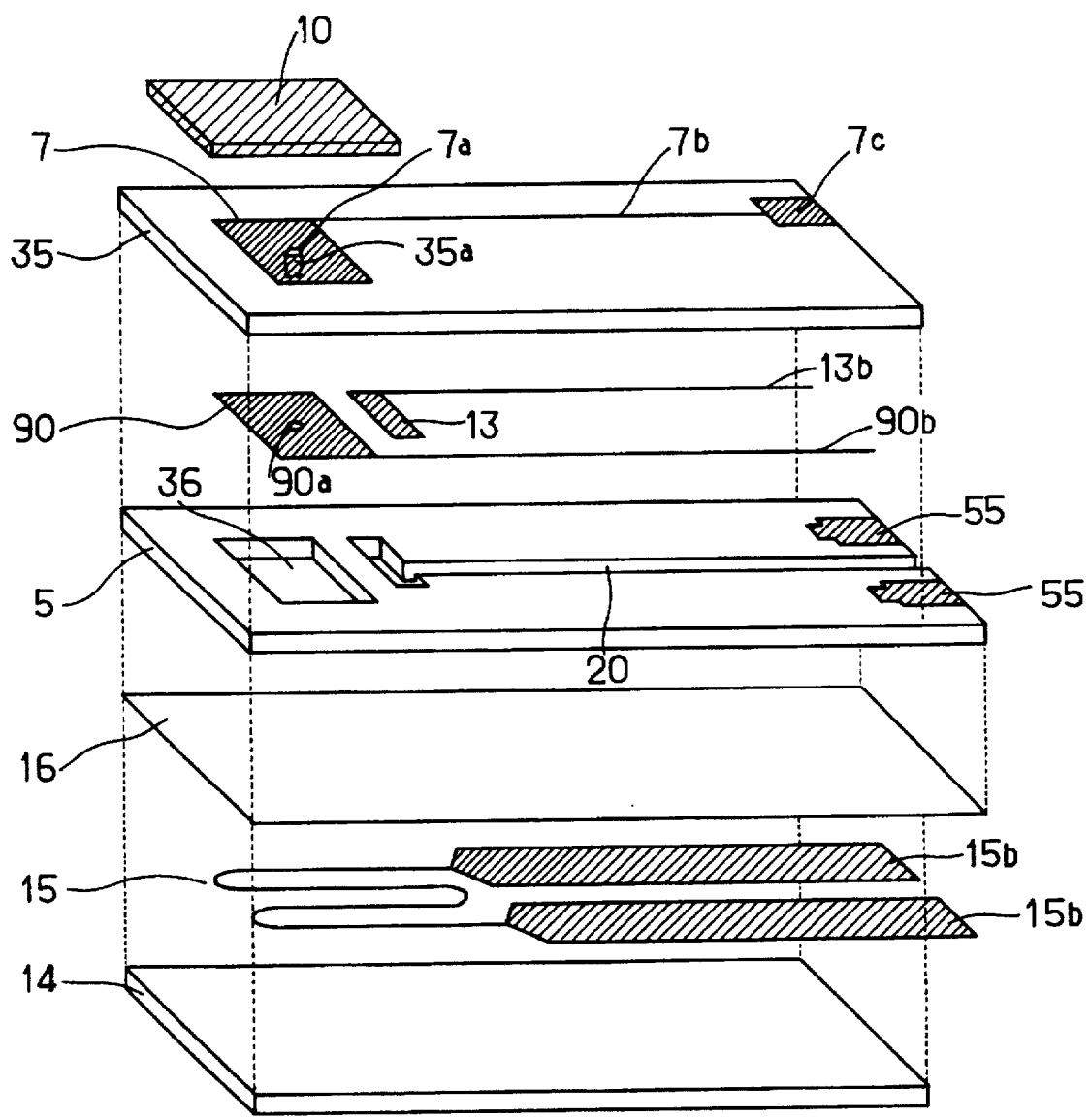
FIG. 23 is a schematic exploded view of the air-fuel ratio detecting element according to the eleventh embodiment of the present invention.

Eleventh embodiment:

An air-fuel ratio detecting element according to an eleventh embodiment of the present invention will now be described with reference to FIG. 22 and FIG. 23. In the air-fuel ratio detecting element of the present embodiment, an electrode of the oxygen pump portion 2 in the inner space 17 and an electrode of the oxygen sensor portion 3 in the inner space 17 are integrated into one common electrode 90. The electrodes 7, 90, 13 are formed on the same solid electrolyte sheet 35. An idea of this present embodiment is explained in control circuit of FIG. 20.

In the first to ninth embodiments, terminals A and B connects with the electrodes of the oxygen sensor portion 3. The electrode 13 (exposed to the air passage 19) of the oxygen sensor portion 3 is connected to terminal A. The electrode 12 (exposed to the inner space 17) of the oxygen sensor portion 3 is connected to terminal B. Terminals C and D connect with the electrodes of the oxygen pump portion 2. The electrode 7 (exposed to gas to be measured) of the oxygen pump portion 2 is connected to terminal C. The electrode 8 (exposed to the inner space 17) of the oxygen pump portion 2 is connected to terminal D. Since the terminal B connecting with the electrode 12 and the terminal D connecting with the electrode 8 are commonly led to the ground. Further, the electrodes 8 and 12 are both disposed in the inner space 17 along the solid electrolyte sheet 35 on the same side. Therefore, in stead of using two electrodes 8 and 12 which are led to the ground, the present embodiment adopts one common electrode 90 as common electrode for the oxygen pump portion 2 and the oxygen sensor portion 3 in the inner space 17. According to the reduction of the number of the electrode, the number of the terminal 55 also reduced. Two terminals 55 are disposed on the spacer 5 as shown in FIG. 22 and FIG. 23, the electrode 13 of the oxygen sensor portion 3 and the electrode 90 of both the oxygen pump and sensor portion 2 and 3 are connected through corresponding leads 13b and 90b to the terminals 55 which are formed on the end portion of the spacer 5.

The solid electrolyte sheet 35 has a hole 35a, and the electrodes 7, 90 have holes 7a, 90a, respectively, the holes being positioned so as to align with each other. The holes 35a, 7a, 90a form a communication hole 9 which passes through the oxygen pump portion 2 and serves as diffusion resisting means. To prevent the communication hole 9 from being clogged with powder such as soot contained in gas to be measured, a porous ceramic protector 10 is provided so as to cover the entire electrode 7.

The spacer 5 is longer than the substrate 14 of the heating element 4 and the solid electrolyte sheet 35, whereby the terminals 55 can be provided for external connections.

The substrate 16 of the heating element 4 has the same length as that of the spacer 5 but longer than the substrate 14, so that the leads 15b of the heating member 15 disposed between the substrate 14 and the substrate 16 are exposed, whereby the leads 15b become connectable. The electrode 7 of the oxygen pump portion 2 is connected to the terminal 7c which is formed on the solid electrolyte sheet 35 at an end corner.

The effects of the eleventh embodiment will now be described.

By commonly using one electrode 90 for the oxygen pump and sensor portion, the number of parts such as electrode, lead wire and terminal are reduced, causing a reduction of production cost. Further, the number of assembly is also reduced when fabricated.

Modification:

In the air-fuel ratio detecting element 1 according to the first embodiment of FIG. 1 for example, a positioning substrate made of an electrical insulating ceramic material such as alumina may be attached to the outer surface of the solid electrolyte sheet 35 and to the outer surface of the substrate 14 of the heating element 4, at the right-hand end portion of the air-fuel ratio detecting element 1 as viewed in FIG. 1 (the open end of the air passage 19). The positioning substrates function to position the air-fuel ratio detecting element 1 in the insulating member 33 shown in FIG. 3.

According to the embodiments given herein, the communication hole which serves as diffusion resisting means for taking gas to be measured in the inner space 17 is located where electrodes of the oxygen pump portion are situated. The location of the communication hole is not limited thereto. The communication hole may be located at any other portion in so far as gas to be measured can be taken into the inner space. For example, in the first embodiment, the communication hole may be a through-hole which is formed in the spacer. In the ninth embodiment, the communication hole may be a through-hole which is formed at a location where an electrode of the oxygen sensor portion is disposed for exposure to the inner space.

According to the embodiments give herein, one communication hole is provided. However, the number of communication holes is not to be limited to one, but may be more than one.

According to the embodiments given herein, when the communication hole is used as diffusion resisting means for gas to be measured, a hole is prepared in each of the electrode of the oxygen pump portion and the solid electrolyte sheet, and thus prepared holes are aligned when stacked, whereby the communication hole is formed in the oxygen pump portion. The method of forming the communication hole, however, is not limited thereto. After the electrode of the oxygen pump portion is superposed on the solid electrolyte sheet, a hole may be prepared through the electrode and the solid electrolyte sheet to form the communication hole.

According to the embodiments given herein, yttria-added zirconia is used as a material for the solid electrolyte sheet which conducts oxygen ions. However, an oxide such as ceria or hafnia may be used instead of zirconia.

According to the embodiments given herein, electrodes of the oxygen sensor portion and the oxygen pump portion are made of platinum and formed by screen-printing. Material and a forming method for the electrodes, however, are not to be limited to them. Gold may be used as material for the electrodes. Also, thin-film techniques such as plating, vapor deposition and the like may be applicable.

According to the embodiments given herein, alumina is used as material for the spacer. Material for the spacer, however, is not to be limited to alumina. Electrical insulating materials such as mullite and spinel may be applicable.

According to the embodiments given herein, alumina is used as material for the porous ceramic protector. Material for the protector, however, is not to be limited to alumina. Ceramic insulating materials such as mullite, spinel and the like may be applicable. Also, according to the embodiments given herein, the protector is formed by applying paste. The method of forming the protector, however, is not to be limited to this. The protector may be formed by screen-printing, plasma spraying, dipping or the like.

According to the ninth embodiment, the oxygen pump portion and the oxygen sensor portion are disposed on opposite sides of the heating element at one end where an opening is formed, whereby the inner space is defined between the oxygen pump portion and the oxygen sensor portion with the opening as an integral part thereof. In this case, the shape and area of the opening in the heating element is arbitrary. What is required is to define the inner space between the oxygen pump portion and the oxygen sensor portion with the opening as an integral part thereof.

According to the second embodiment, alumina is used as material for the volume adjusting member. Material for the volume adjusting member, however, is not to be limited to alumina. Ceramic insulating materials such as magnesia, alumina spinel, zirconia and cordierite may be applicable. Also, according to the second embodiment, a formed material is fit into the opening in the spacer. The method of making the volume adjusting member, however, is not to be limited to this. Also, it is possible to prepare a paste including an electrical insulating material and apply it into the opening.

According to the embodiments given herein, the manufacture of air-fuel ratio detecting elements undergo steps of layering, thermocompression bonding the stacked assembly, baking the thermocompression bonded assembly, and dividing the baked assembly into individual elements. The manufacturing procedure, however, is not to be limited to this. The baking step may come after the dividing step.

To reduce the number of output terminals of the air-fuel ratio detecting device for simplifying the structure thereof, for example, the electrode 8 of the oxygen pump portion 2 and the electrode 12 of the oxygen sensor portion 3 may share an output terminal. In this case, there electrodes may be joined together within the air-fuel ratio detecting element 1 or outside the air-fuel ratio detecting element 1, i.e. within the housing.

Also, according to the embodiments given herein, lead wires are connected to the output terminals of the air-fuel ratio detecting element by brazing. The method of connecting the lead wires to the output terminals, however, is not to be limited to brazing. The lead wires may be brought in contact with the output terminals by using plate springs or the like, or may be fixed by caulking.

According to the embodiments given herein, leads, terminals, and a heating element are formed on the solid electrolyte sheet 35. In actual detecting elements, a thin film (not shown) of electrical insulating ceramic such as alumina is formed on the solid electrolyte sheet 35, and the leads, terminals, and heating element are formed thereon. The reason for this is to prevent a leak current from flowing between structural elements through the solid electrolyte sheet 35.

What is claimed is:

1. An air-fuel ratio detecting device, comprising:
   a solid electrolyte sheet;
   a ceramic insulating sheet which is opposed to said solid electrolyte sheet;
   a means for forming an inner space between said solid electrolyte sheet and said insulating sheet and which communicates with gas to be measured;
   a means for forming a reference oxygen space which is defined along said solid electrolyte sheet and separated from said inner space and in which a substance containing reference oxygen is led;
   a first pair of electrodes which is provided on said solid electrolyte sheet, said electrodes being disposed apart from each other;
   an oxygen pump portion which is composed of said solid electrolyte sheet and said first pair of electrodes, one of said electrodes being exposed to said inner space and the other of said electrodes being exposed to gas to be measured;
   a second pair of electrodes which is provided on said solid electrolyte sheet, said electrodes being disposed apart from each other; and
   an oxygen sensor portion which is composed of said solid electrolyte sheet and said second pair of electrodes, one of said electrodes being exposed to said inner space and the other of said electrodes being exposed to said reference oxygen space.

2. An air-fuel ratio detecting device according to claim 1, wherein one of said first pair of electrodes exposed to said inner space and one of said second pair of electrodes exposed to said inner space forms one electrode exposed to said inner space.

3. An air-fuel ratio detecting device according to claim 1, wherein said insulating sheet is provided with a heating member for heating said solid electrolyte sheet.

4. An air-fuel ratio detecting device according to claim 1, wherein a communication hole is formed in said solid electrolyte sheet for establishing communication between said inner space and gas to be measured.

5. An air-fuel ratio detecting device according to claim 1, wherein said reference oxygen space and said inner space are defined between said solid electrolyte sheet and said insulating sheet, and an isolating member is disposed between said solid electrolyte sheet and said insulating sheet for isolating said reference oxygen space from said inner space.

6. An air-fuel ratio detecting device according to claim 5, wherein said first pair of electrodes of said oxygen pump portion is formed on said solid electrolyte sheet such that one of said electrodes is formed on a first side of said solid electrolyte sheet and the other of said electrodes is formed on a second side which is opposite to the first side and is exposed to gas to be measured, said second pair of electrodes of said oxygen sensor portion is formed on the first side of said solid electrolyte sheet to be separated from each other, and the isolating member is located between said electrodes of said oxygen sensor portion.

7. An air-fuel ratio detecting device according to claim 1 or 6, wherein a slit is formed in said solid electrolyte sheet across the width thereof such that said slit is located between said oxygen pump portion and said oxygen sensor portion, the slit being shorter than the width of said solid electrolyte sheet.

8. An air-fuel ratio detecting device according to claim 5, wherein said first pair of electrodes of said oxygen pump portion and said second pair of electrodes of said oxygen sensor portion are all formed on the first side of said solid electrolyte sheet.

9. An air-fuel ratio detecting device according to claim 5, wherein a volume adjusting member is fixed on said insulating sheet at a portion corresponding to said inner space for adjusting the volume of said inner space.

10. An air-fuel ratio detecting device according to claim 1, wherein air is led into said reference oxygen space.

11. An air-fuel ratio detecting device according to claim 1, wherein said oxygen sensor portion generates an output based on the difference in oxygen concentration between said inner space and said reference oxygen space, and said oxygen pump portion functions to maintain a set oxygen concentration in said inner space, whereby a current corresponding to the concentration of oxygen in gas to be measured flows through said oxygen pump portion.

12. An air-fuel ratio detecting device, comprising:
   a solid electrolyte sheet;
   a heating element sheet which includes two ceramic insulating sheets and an electrical heating member held between said ceramic insulating sheets and which is opposed to said solid electrolyte sheet;
   a ceramic sheet insulating spacer which is disposed between said heating element sheet and said solid electrolyte sheet, which defines an inner space communicating with gas to be measured between said heating element sheet and said solid electrolyte sheet, and which functions to define a reference oxygen space which is isolated from the inner space and in which a substance containing reference oxygen exists;
   a pair of electrodes which is provided on said solid electrolyte sheet, said electrodes being disposed apart from each other;
   an oxygen pump portion which is composed of said solid electrolyte sheet and said pair of electrodes, one of said electrodes being exposed to the inner space and the other of said electrodes being exposed to gas to be measured;
   another pair of electrodes which is provided on said solid electrolyte sheet, said electrodes being disposed apart from each other; and
   an oxygen sensor portion which is composed of said solid electrolyte sheet and said another pair of electrodes, one of said electrodes being exposed to the inner space and the other of said electrodes being exposed to the reference oxygen space.

13. An air-fuel ratio detecting device according to claim 12, wherein one of said a first pair of electrodes exposed to said inner space and one of said a second pair of electrodes exposed to said inner space forms one electrode exposed to said inner space.

14. An air-fuel ratio detecting device according to claim 12, wherein said insulating spacer integrally includes an opening which functions to define said inner space, an opening which functions to define the reference oxygen space, and an isolating portion which is located between the openings for isolating them from each other.

15. An air-fuel ratio detecting device according to claim 14, wherein said solid electrolyte sheet has a first side opposed to said heating element sheet and a second side which is opposite to the first side and is exposed to gas to be measured, said pair of electrodes of said oxygen pump portion is formed on said solid electrolyte sheet such that one of said electrodes is formed on the first side of said solid electrolyte sheet and the other of said electrodes is formed on the second side, said another pair of electrodes of said oxygen sensor portion is formed on the first side of said solid electrolyte sheet, and the isolating portion of said insulating spacer is located between said electrodes of said oxygen sensor portion for isolating them from each other.

16. An air-fuel ratio detecting device according to claim 15, wherein a communication hole is formed in said solid electrolyte sheet for establishing communication between the inner space and gas to be measured and wherein said electrodes of said oxygen pump portion are disposed around the communication hole.

17. An air-fuel ratio detecting device according to claim 12, wherein air is led into the reference oxygen space.

18. An air-fuel ratio detecting device according to claim 12, wherein said oxygen sensor portion generates an output based on the difference in oxygen concentration between the inner space and the reference oxygen space and wherein said oxygen pump portion functions to maintain a set oxygen concentration in the inner space, whereby a current corresponding to the concentration of oxygen in gas to be measured flows through said oxygen pump portion.

19. An air-fuel ratio detecting device, comprising:

a solid electrolyte sheet;

a ceramic insulating sheet which is opposed to said solid electrolyte sheet;

a means for forming an inner space between said solid electrolyte sheet and said insulating sheet and which communicates with gas to be measured;

a means for forming a reference oxygen space which is defined along said solid electrolyte sheet and separated from said inner space and in which reference oxygen is led;

an oxygen pump portion composed of said electrolyte sheet and an electrode formed on said electrolyte sheet and for moving oxygen between said gas to be measured and said inner space;

an oxygen sensor portion composed of said electrolyte sheet and an electrode formed on said electrolyte sheet and for generating a signal based on a difference of oxygen concentration between said inner space and said reference oxygen space.

20. An air-fuel ratio detecting device according to claim 19, wherein said pump portion maintains a certain oxygen concentration in said inner space based on said signal generated by said oxygen sensor portion so that an electric current responding to oxygen concentration in said gas to be measured flows in said oxygen pump portion.

* * * * *